(12) United States Patent
Hirst et al.

(10) Patent No.: US 7,071,199 B1
(45) Date of Patent: Jul. 4, 2006

(54) KINASE INHIBITORS AS THERAPEUTIC AGENTS

(75) Inventors: Gavin C. Hirst, Marlborough, MA (US); Paul Rafferty, Westborough, MA (US); Kurt Ritter, Newton, MA (US); David Calderwood, Farmingham, MA (US); Helen Twigger, Nottingham (GB); Stephen St. Gallay, Loughborough (GB)

(73) Assignee: Abbott GmbH & CCo. KG, Wiesbaden (DE)

( * ) Notice: Subject to any disclaimer, the term of this patent is extended or adjusted under 35 U.S.C. 154(b) by 0 days.

(21) Appl. No.: 09/663,320

(22) Filed: Sep. 15, 2000

Related U.S. Application Data

(60) Provisional application No. 60/154,618, filed on Sep. 17, 1999.

(51) Int. Cl.
*C07D 487/04* (2006.01)

(52) U.S. Cl. ...................... 514/258; 544/280
(58) Field of Classification Search ................ 544/280; 514/258
See application file for complete search history.

(56) References Cited

U.S. PATENT DOCUMENTS

| | | | |
|---|---|---|---|
| 4,140,851 A | 2/1979 | Townsend | 536/24 |
| 4,229,453 A | 10/1980 | Roth et al. | 424/251 |
| 4,892,865 A | 1/1990 | Townsend et al. | 514/43 |
| 4,927,830 A | 5/1990 | Townsend et al. | 514/258 |
| 4,968,686 A | 11/1990 | Townsend et al. | 514/258 |
| 4,996,206 A | 2/1991 | Taylor et al. | 514/258 |
| 5,028,608 A | 7/1991 | Taylor et al. | 514/258 |
| 5,248,775 A | 9/1993 | Taylor et al. | 544/280 |
| 5,254,687 A | 10/1993 | Taylor et al. | 544/280 |
| 5,344,932 A | 9/1994 | Taylor | 544/280 |
| 5,349,064 A | 9/1994 | Akimoto et al. | 544/280 |
| 5,416,211 A | 5/1995 | Barnett et al. | 544/280 |
| 5,593,997 A | 1/1997 | Dow et al. | 514/258 |
| 5,594,121 A | 1/1997 | Froehler et al. | 536/23.5 |
| 5,612,482 A | 3/1997 | Barnett et al. | 544/280 |
| 5,639,757 A | 6/1997 | Dow et al. | 514/261 |
| 5,644,057 A | 7/1997 | Yuan et al. | 544/280 |
| 5,644,058 A | 7/1997 | Barnett et al. | 544/280 |
| 5,665,721 A | 9/1997 | Bhagwat et al. | 514/253 |
| 5,686,457 A | 11/1997 | Traxler et al. | 514/258 |
| 5,721,356 A | 2/1998 | Ugarkar et al. | 536/27.2 |
| 5,726,302 A | 3/1998 | Ugarkar et al. | 536/27.13 |
| 5,763,596 A | 6/1998 | Boyer et al. | 536/27.13 |
| 5,763,597 A | 6/1998 | Ugarkar et al. | 536/27.13 |
| 5,834,469 A | 11/1998 | Elliott et al. | 514/249 |

FOREIGN PATENT DOCUMENTS

| | | |
|---|---|---|
| DE | 3036390 | 5/1982 |
| EP | 0402903 | 12/1990 |
| EP | 0496617 | 7/1992 |
| EP | 0795556 | 9/1997 |
| WO | 94/17803 | 8/1994 |
| WO | 96/10028 | 4/1996 |
| WO | 96/31510 | 10/1996 |
| WO | 96/40686 | 12/1996 |
| WO | 96/40705 | 12/1996 |
| WO | 96/40706 | 12/1996 |
| WO | 96/40707 | 12/1996 |
| WO | 96/02266 | 1/1997 |
| WO | 97/03069 | 1/1997 |
| WO | 97/13771 | 4/1997 |
| WO | 97/28161 | 8/1997 |
| WO | 97/32879 | 9/1997 |
| WO | 97/34895 | 9/1997 |
| WO | WO 97/49706 | * 12/1997 |
| WO | 98/41525 | 9/1998 |
| WO | 00/44728 | 8/2000 |

OTHER PUBLICATIONS

Hanke, J.H. et al., "Discovery of a Novel, Potent and Src Family-selective Tyrosine Kinase Inhibitor", J. Biol. Chem., 271(2):695-701, (1996).

Missbach, M. et al., "A Novel Inhibitor of the Tyrosine Kinase Src Suppresses Phosphorylation of its Major Cellular Substrates and Reduces Bone Resorption In Vitro and in Rodent Models In Vivo", Bone, 24(5):437-449. (1999).

Traxler, P.M. et al., "4-(Phenylamino)pyrrolopyrimidines: Potent and Selective, ATP Site Directed Inhibitors of the EGF-Receptor Protein Tyrosine Kinase", J. Med. Chem., 39: 2285-2292, (1996).

Showlater, H.D.H. et al., "Synthesis and SAR for a Series of 4-substituted 1H-pyrimido [4,5-b] and SH-pyrimido [5, 4-b] indoles as EGF Receptor Tyrosine Kinase Inhibitors", Proceedings of the American Association for Cancer Research, 37, Mar. 1996, (abstract).

Dave, C.G. et al., "Synthesis & Biological Activity of Pyrrolo[2, 3-d] Pyrimidines", Indian J. Chem., 27B:778-780, (1988).

* cited by examiner

*Primary Examiner*—Bruck Kifle
(74) *Attorney, Agent, or Firm*—John D. Conway; Gayle B. O'Brien

(57) ABSTRACT

The present application is directed to a compound of Formula (I) as defined herein which are useful as kinase inhibitors.

69 Claims, No Drawings

KINASE INHIBITORS AS THERAPEUTIC AGENTS

RELATED APPLICATION

This application claims the benefit of U.S. Provisional Application No. 60/154,618, filed Sep. 17, 1999, the entire teachings of which are incorporated herein by reference.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990).

The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):11–15, 1993). DNAs encoding mouse, rat and human FLK-1 have been isolated, and the nucleotide and encoded amino acid sequences reported (Matthews et al., *Proc. Natl. Acad. Sci.*

USA, 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989–991, 1992; Shibuya et al., *Oncogene* 5:519–524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine &Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848–859, 1993; Kolch et al., *Breast Cancer Research and Treatment* 36: 139–155, 1995; Ferrara et al., *Endocrine Reviews* 18(1); 4–25, 1997; Ferrara et al., *Regulation of Angiogenesis* (ed. L. D. Goldberg and E. M. Rosen), 209–232, 1997). In addition, VEGF has been implicated in the control and enhancement of vascular permeability (Connolly, et al., *J. Biol. Chem.* 264: 20017–20024, 1989; Brown et al., *Regulation of Angiogenesis* (ed. L. D. Goldberg and E. M. Rosen), 233–269, 1997).

Different forms of VEGF arising from alternative splicing of mRNA have been reported, including the four species described by Ferrara et al. (*J. Cell. Biochem.* 47:211–218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.,* 159–164, 1998 and references cited therein).

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395–403; Witzenbichler et al, *Am. J. Pathol.* (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14),8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363–374; Ogawa et al, *J. Biol. Chem.* (1998), 273(47), 31273–31282.). VEGF-E sequences possess 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120 (1997)). Until now, no direct evidence for the essential role of KDR in VEGF-mediated vascular hyperpermeability has been disclosed.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Application No. 4,966,849), soluble receptors and antibodies (Application No. WO 94/10202; Kendall & Thomas, 1994, *Proc. Natl. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is Also Known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides a compound of Formula (I), the racemic-diastereomeric mixtures, optical isomers, pharmaceutically-acceptable salts, prodrugs or biologically active metabolites thereof, selected from the group consisting of sub-formulas 1–109:

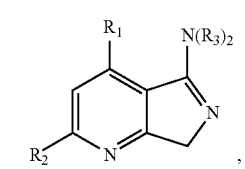

-continued
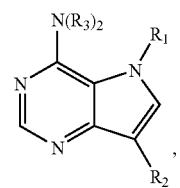
2
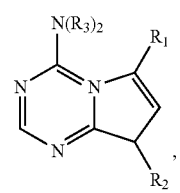
3
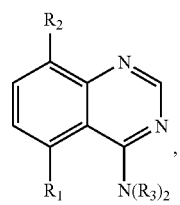
4
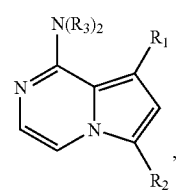
5
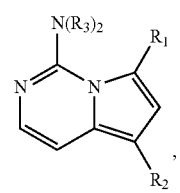
6
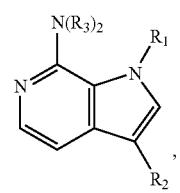
7
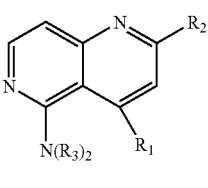
8
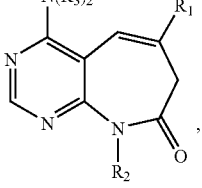
9
-continued
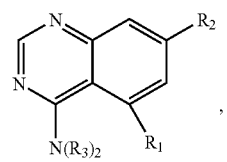
10
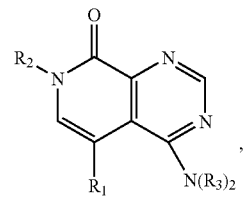
11
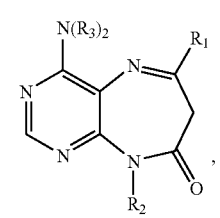
12
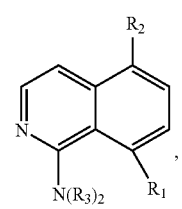
13
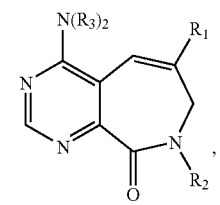
14
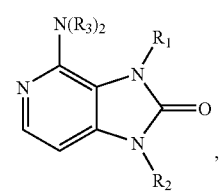
15
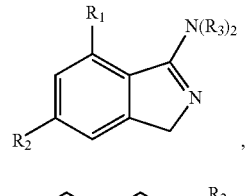
16
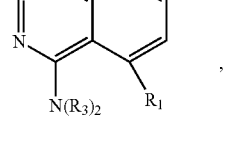
17

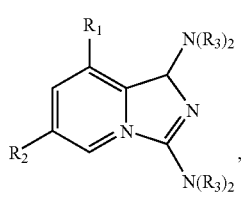
18
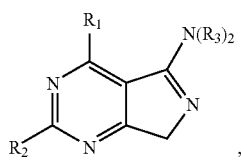
19
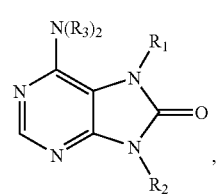
20
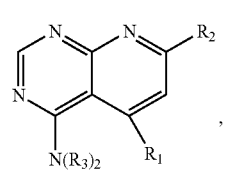
21
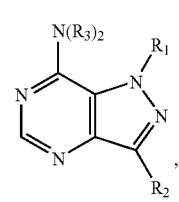
22
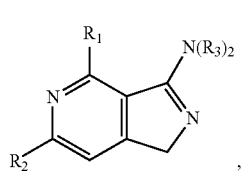
23
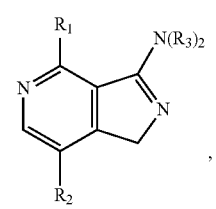
24
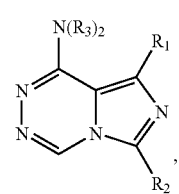
25
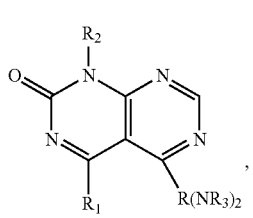
26
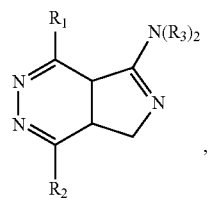
27
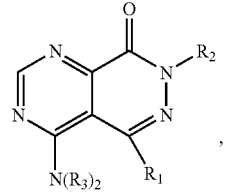
28
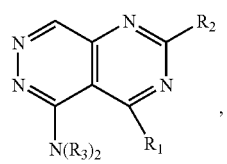
29
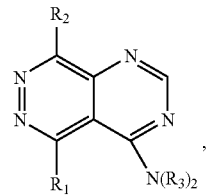
30
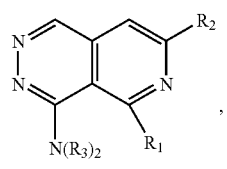
31
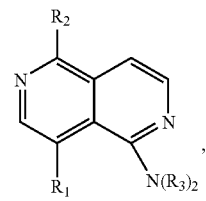
32
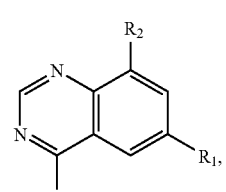
33

-continued

-continued
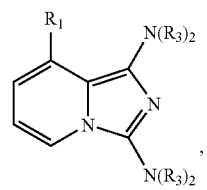
50
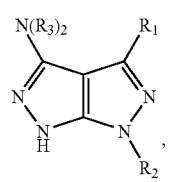
51
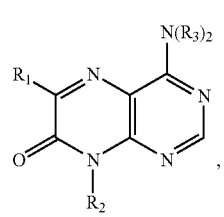
52
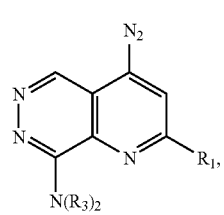
53
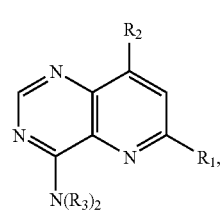
54
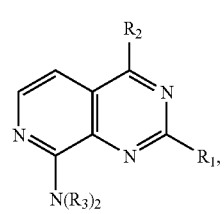
55
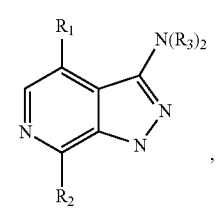
56
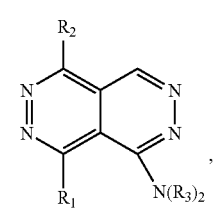
57
-continued
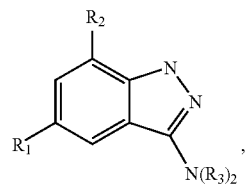
58
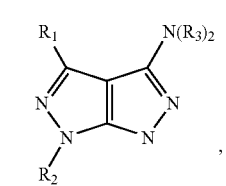
59
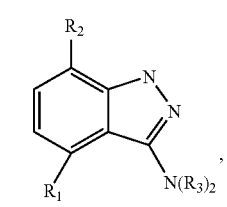
60
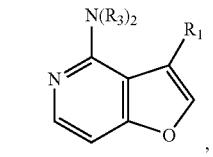
61
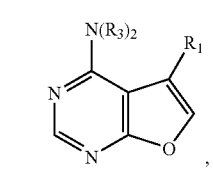
62
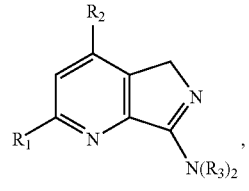
63
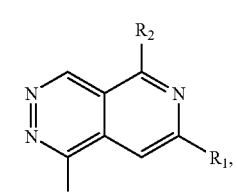
64
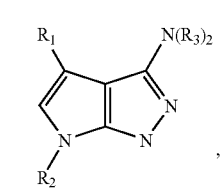
65

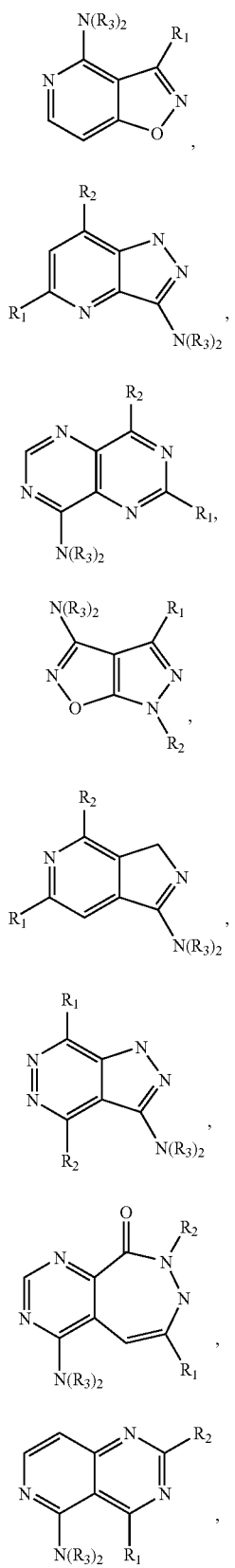
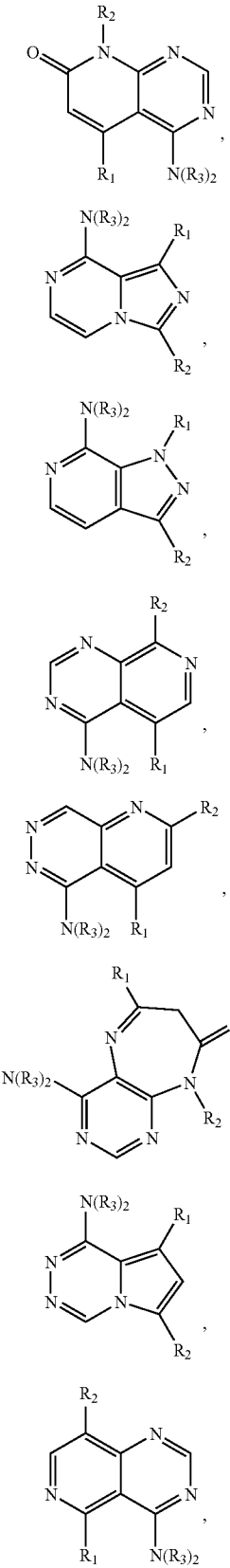

-continued
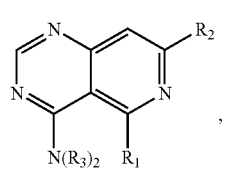
82
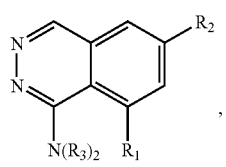
83
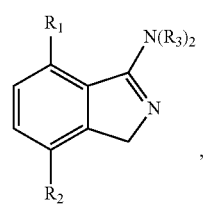
84
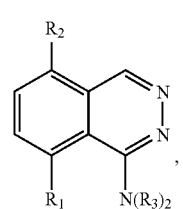
85
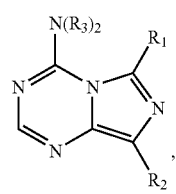
86
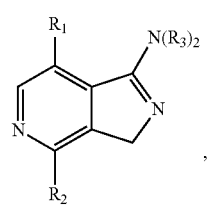
87
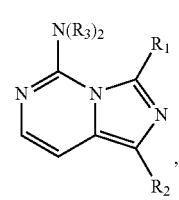
88
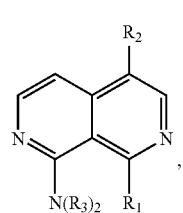
89
-continued
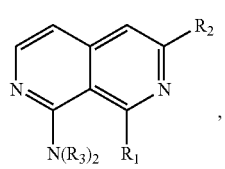
90
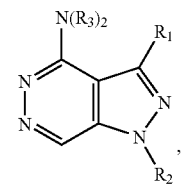
91
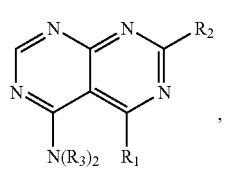
92
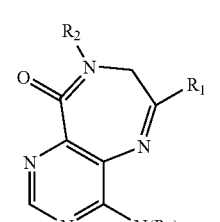
93
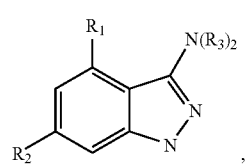
94
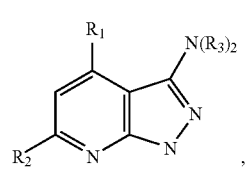
95
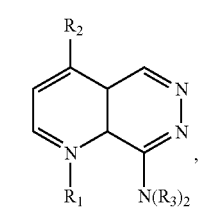
96
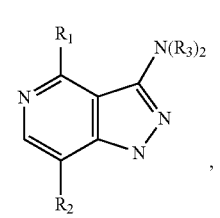
97

-continued
98 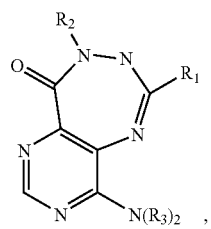
99 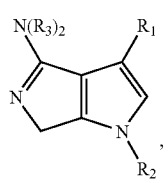
100 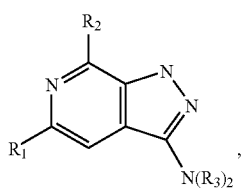
101 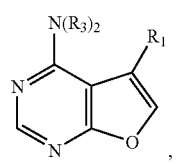
102 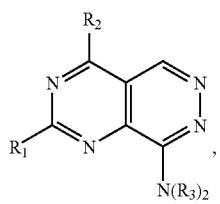
103 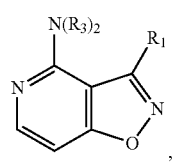
104 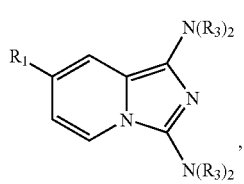
105 
-continued
106 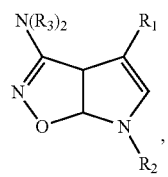
107 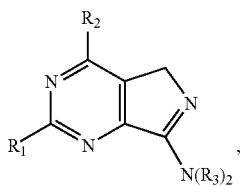
108 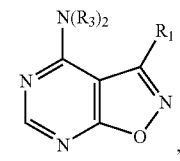
109 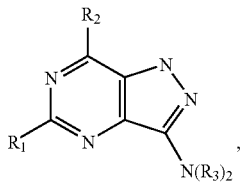
110 
111 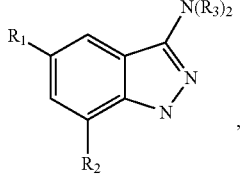
112 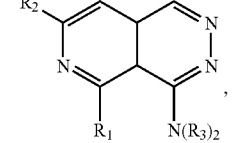
113 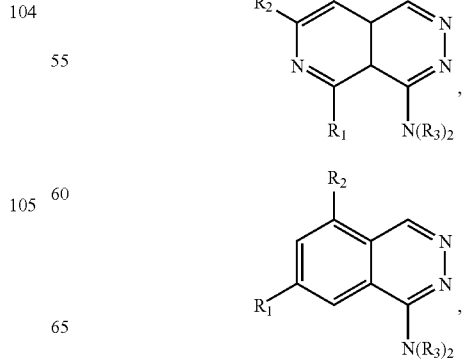

-continued

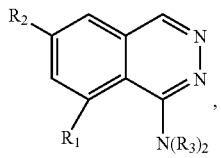
114

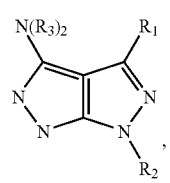
115

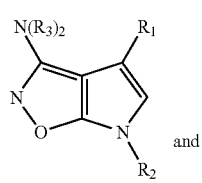
116
and

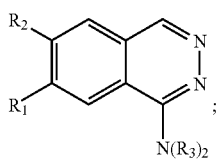
117

$R_1$ is of the formula

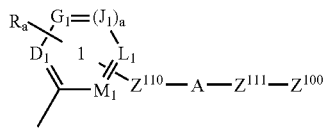

where $Z^{100}$ is

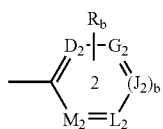

or a group optionally substituted with $R_b$ selected from the group consisting of cycloalkyl, naphthyl, tetrahydronaphthyl, benzothienyl, furanyl, thienyl, benzoxazolyl, benzothiazolyl,

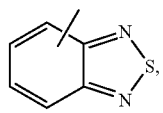

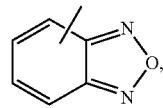

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted ($C_1$–$C_6$) which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted ($C_1$–$C_6$) or an optionally substituted —$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_b$ each represent one or more substituents for each occurrence independently selected from the group consisting of hydrogen, halogen, —CN, —$NO_2$, —C(O)OH, —C(O)H, —OH, —C(O)O-alkyl, substituted or unsubstituted carboxamido, tetrazolyl, trifluoromethylcarbonylamino, trifluoromethylsulfonamido, substituted or unsubstituted alkyl, substituted or unsubstituted alkoxy, substituted or unsubstituted aryl, substituted or unsubstituted alkenyl, substituted or unsubstituted aryloxy, substituted or unsubstituted heteroaryloxy, substituted or unsubstituted arylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -$Z^{105}$-C(O)N(R)$_2$, -$Z^{105}$-N(R)—C(O)-$Z^{200}$, -$Z^{105}$—N(R)—S(O)$_2$-$Z^{200}$, -$Z^{105}$—N(R)—C(O)—N(R)-$Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—Oalkyl, —W—$(CH_2)_t$—S-alkyl, or —W—$(CH_2)_t$—OH;

$Z^{105}$ for each occurrence is independently a covalent bond or ($C_1$–$C_6$);

$Z^{200}$ for each occurrence is independently a substituted or unsubstituted ($C_1$–$C_6$), substituted or unsubstituted phenyl or substituted or unsubstituted —($C_1$–$C_6$)-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring; t for each occurrence is independently an integer from 2 to 6; W for each occurrence is independently a direct bond or O, S, S(O), S(O)$_2$, or $NR_f$, wherein $R_f$ for each occurrence is independently H or alkyl; or $R_1$ is a substituted or unsubstituted carbocyclic or heterocyclic ring fused with ring 2;

A is —O—; —S—; —S(O)$_p$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR); —CH=CH—; —C(=NOR)—; —C(O)—; —CH(OR)—; —C(O)N(R)—; —N(R)C(O)—; —N(R)S(O)$_p$—; —OC(O)N(R)—; ; —N(R)—C(O)—(CH$_2$)$_m$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_g$)O—; —N(R)P(OR$_g$)—; —N(R)P(O)(OR$_g$)O—; —N(R)P(O)(OR$_g$)—; —N(C(O)R)P(OR$_g$)O—; —N(C(O)R)P(OR$_g$)—; —N(C(O)R)P(O)(OR$_g$)O—, or —N(C(O)R)P(OR$_g$)—;

where R for each occurrence is independently H, substituted or unsubstituted alkyl, substituted or unsubstituted arylalkyl or substituted or unsubstituted aryl;

R$_g$ for each occurrence is independently H, substituted or unsubstituted alkyl, substituted or unsubstituted arylalkyl, substituted or unsubstituted cycloalkyl or substituted or unsubstituted aryl;

p is 1 or 2;

or in a phosphorus containing group, the nitrogen atom, the phosphorus atom, R and R$_g$ together form a five- or six-membered heterocyclic ring; or A is NRSO$_2$ and R, R$_a$ and the nitrogen atom together form a substituted or unsubstituted five or -six-membered heterocyclic ring fused to ring 1;

R$_2$ is -Z$^{101}$-Z$^{102}$;

Z$^{101}$ is a covalent bond, —(C$_1$–C$_6$)—, —(C$_1$–C$_6$)—O—, —(C$_1$–C$_6$)—C(O)—, —(C$_1$–C$_6$)—C(O)O—, —(C$_1$–C$_6$)—C(O)—NH—, —(C$_1$–C$_6$)—C(O)—N((C$_1$–C$_6$))— or a substituted or unsubstituted phenyl group;

Z$^{102}$ is hydrogen, a substituted or unsubstituted alkyl group, a substituted or unsubstituted cycloalkyl group, a substituted or unsubstituted, saturated or unsaturated heterocyclic group, or a substituted or unsubstituted, saturated or unsaturated heterobicyclic group;

said substituted heterocyclic or substituted heterobicyclic group having one or more substituents each independently selected from the group consisting of hydroxyl, cyano, substituted or unsubstituted alkoxy, substituted or unsubstituted sulfonamido, substituted or unsubstituted ureido, substituted or unsubstituted carboxamido; substituted or unsubstituted amino, oxo, a saturated, unsaturated or aromatic, substituted or unsubstituted heterocyclic group comprising one or more nitrogen atoms, one or more oxygen atoms or a combination thereof;

wherein said nitrogen atoms are independently optionally substituted by a substituted or unsubstituted alkyl, substituted or unsubstituted aryl or substituted or unsubstituted arylalkyl group; or R$_2$ is of the formula B-E, wherein B is a substituted or unsubstituted cycloalkyl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalklylcarbonyl, hydroxy, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted azacycloalkyl, substituted or unsubstituted azacycloalkylcarbonyl, substituted or unsubstituted azacycloalkylsulfonyl, substituted or unsubstituted azacycloalkylalkyl, substituted or unsubstituted heteroaryl, substituted or unsubstituted heteroarylcarbonyl, substituted or unsubstituted heteroarylsulfonyl, substituted or unsubstituted heteroarylalkyl, substituted or unsubstituted azacycloalkylcarbonylamino, substituted or unsubstituted heteroarylcarbonylamino or substituted or unsubstituted aryl;

R$_3$ for each occurrence is independently hydrogen, hydroxy, substituted or unsubstituted alkyl or substituted or unsubstituted alkoxy;

a is 1 and D$_1$, G$_1$, J$_1$, L$_1$ and M$_1$ are each independently selected from the group consisting of CR$_a$ and N, provided that at least two of D$_1$, G$_1$, J$_1$, L$_1$ and M$_1$ are CR$_a$; or a is 0, and one of D$_1$, G$_1$, L$_1$ and M$_1$ is NR$_a$, one of D$_1$, G$_1$, L$_1$ and M$_1$ is CR$_a$ and the remainder are independently selected from the group consisting of CR$_a$ and N, wherein R$_a$ is as defined above;

b is 1 and D$_2$, G$_2$, J$_2$, L$_2$ and M$_2$ are each independently selected from the group consisting of CR$_a$ and N, provided that at least two of D$_2$, G$_2$, J$_2$, L$_2$ and M$_2$ are CR$_a$; or b is 0, and one of D$_2$, G$_2$, L$_2$ and M$_2$ is NR$_a$, one of D$_2$, G$_2$, L$_2$ and M$_2$ is CR$_a$ and the remainder are independently selected from the group consisting of CR$_a$ and N, wherein R$_a$ is as defined above; and n for each occurrence is independently an integer from 0 to 6.

Each of the sub-formulas 1–117 is a preferred embodiment of the present application.

The compounds of this invention are useful as inhibitors of serine/threonine and tyrosine kinases. In particular, compounds of this invention are useful as inhibitors of tyrosine kinases that are important in hyperproliferative diseases, especially in cancer and in the process of angiogenesis. For example, certain of these compounds are inhibitors of such receptor kinases as KDR, Flt-1, FGFR, PDGFR, c-Met, TIE-2 or IGF-1-R. Since certain of these compounds are anti-angiogenic, they are important substances for inhibiting the progression of disease states where angiogenesis is an important component. Certain compounds of the invention are effective as inhbitors of such serine/threonine kinases as PKCs, erk, MAP kinases, cdks, Plk-1 or Raf-1. These compounds are useful in the treatment of cancer, and hyperproliferative disorders. In addition, certain compounds are effective inhibitors of non-receptor kinases such as those of the Src (for example, lck, blk and lyn), Tec, Csk, Jak, Map, Nik and Syk families. These compunds are useful in the treatment of cancer, hyperproliferative disorders and immunologic diseases.

Certain compounds of this invention are selective TIE-2 kinase inhibitors which may be anti-angiogenic (especially in combination with one or more VEGFR inhibitors), or pro-angiogenic, when employed in the presence of, or in conjunction with, a VEGF-related stimulus. In this manner such inhibitors can be used in the promotion of therapeutic angiogenesis to treat, for example, ischemia, infarct or occlusion, or to promote wound healing.

The present invention provides a method of inhibiting the kinase activity of tyrosine kinases and serine/threonine kinases comprising the administration of a compound represented by formulas 1–109 to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

DETAILED DESCRIPTION OF THE INVENTION

Progression through the eukaryotic cell cycle is controlled by a family of kinases called cyclin dependent kinases (CDKs) (Myerson et al., *EMBO Journal*, 11:2909–2917 (1992)). The regulation of CDK activation is complex, but requires the association of the CDK with a member of the cyclin family of regulatory subunits (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992)). A further level of regulation occurs through both activating and inactivating phosphorylations of the CDK subunit (Draetta, *Trends in Cell Biology*, 3:287–289 (1993)); Murray and Kirschner, *Nature*, 339: 275–280 (1989); Solomon et al., *Molecular Biology of the Cell*, 3:13–27 (1992); Ducommun et al., *EMBO Journal*, 10:3311–3319 (1991); Gautier et al., *Nature* 339:626–629 (1989); Gould and Nurse, *Nature*, 342:39–45 (1989); Krek and Nigg, *EMBO Journal*, 10:3331–3341 (1991); Solomon et al., *Cell*, 63:1013–1024 (1990)). The coordinate activation and inactivation of different cyclin/CDK complexes is necessary for normal progression through the cell cycle (Pines, *Trends in Biochemical Sciences*, 18:195–197 (1993); Sherr, *Cell*, 73:1059–1065 (1993)). Both the critical G1-S and G 2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066–2076 (1994); Ohtsubo and Roberts, *Science*, 259: 1908–1912 (1993); Quelle et al., *Genes & Development*, 7:1559–1571 (1993); Resnitzky et al., *Molecular & Cellular Biology*, 14:1669–1679 (1994)). Progression through S-phase requires the activity of cyclin A/CDK2 (Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)) whereas the activation of cyclin A/cdc2 (CDK1) and cyclin B/cdc2 are required for the onset of metaphase (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysi-cal Research Communications*, 182:1144–1154 (1992)). It is not surprising, therefore, that the loss of control of CDK regulation is a frequent event in hyperproliferative diseases and cancer. (Pines, *Current Opinion in Cell Biology*, 4:144–148 (1992); Lees, *Current Opinion in Cell Biology*, 7:773–780 (1995); Hunter and Pines, *Cell*, 79:573–582 (1994)). The selective inhibition of CDKs is therefore an object of the present invention.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation, neurodegenerative diseases, macular degeneration, and diabetic retinopathy.

Inhibitors of kinases involved in mediating or maintaining these disease states represent novel therapies for these disorders. Examples of such kinases include, but are not limited to: (1) inhibition of c-Src (Brickell, *Critical Reviews in Oncogenesis*, 3:401–406 (1992); Courtneidge, *Seminars in Cancer Biology*, 5:236–246 (1994), raf (Powis, *Pharmacology &Therapeutics*, 62:57–95 (1994)) and the cyclin-dependent kinases (CDKs) 1, 2 and 4 in cancer (Pines, *Current Opinion in Cell Biology*, 4:144–148 (1992); Lees, *Current Opinion in Cell Biology*, 7:773–780 (1995); Hunter and Pines, *Cell*, 79:573–582 (1994)), (2) inhibition of CDK2 or PDGF-R kinase in restenosis (Buchdunger et al., *Proceedings of the National Academy of Science USA*, 92:2258–2262 (1995)), (3) inhibition of CDK5 and GSK3 kinases in Alzheimers (Hosoi et al., *Journal of Biochemistry* (Tokyo), 117:741–749 (1995); Aplin et al., *Journal of Neurochemistry*, 67:699–707 (1996), (4) inhibition of c-Src kinase in osteoporosis (Tanaka et al., *Nature*, 383:528–531 (1996), (5) inhibition of GSK-3 kinase in type-2 diabetes (Borthwick et al., *Biochemical & Biophysical Research Communications*, 210:738–745 (1995), (6) inhibition of the p38 kinase in inflammation (Badger et al., *The Journal of Pharmacology and Experimental Therapeutics*, 279:1453–1461 (1996)), (7) inhibition of VEGF-R 1–3 and TIE-1 and -2 kinases in diseases which involve angiogenesis (Shawver et al., *Drug Discovery Today*, 2:50–63 (1997)), (8) inhibition of UL97 kinase in viral infections (He et al., *Journal of Virology*, 71:405–411 (1997)), (9) inhibition of CSF-1R kinase in bone and hematopoetic diseases (Myers et al., *Bioorganic & Medicinal Chemistry Letters*, 7:421–424 (1997), and (10) inhibition of Lck kinase in autoimmune diseases and transplant rejection (Myers et al., *Bioorganic & Medicinal Chemistry Letters*, 7:417–420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al, *Cancer Research*, 56:3199–3202 (1996); Kohn et al., *Journal of Cellular Biochemistry*, 54:44–452 (1994)). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275: 523–527 (1997)). NF-kB regulates genes involved in inflammatory responses (such as hematopoetic growth factors, chemokines and leukocyte adhesion molecules) (Baeuerle and Henkel, *Annual Review of Immunology*, 12:141–179 (1994)) and may be involved in the suppression of apoptotic signals within the cell (Beg and Baltimore, *Science*, 274:782–784 (1996); Wang et al., *Science*, 274: 784–787 (1996); Van Antwerp et al., *Science*, 274:787–789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1–7 (1993)). Inhibition of the *Aspergillus* kinases Cdc2/CDC28 or Nim A (Osmani et al., *EMBO Journal*, 10:2669–2679 (1991); Osmani et al., *Cell*, 67:283–291 (1991)) may cause arrest or death in the fungi, improving the therapeutic outcome for patients with these infections.

In one embodiment, the present invention provides compounds of formulas 1–109 as described above. The values of substituents in preferred groups of compounds of formulas 1–109 are given below.

Preferably, $R_b$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted and unsubstituted tetrazolyl, substituted and usubstituted styryl, substituted and unsubstituted arylthio, substituted and unsubstituted heteroarylthio; $CH_2OR_c$, wherein $R_c$ is hydrogen or substituted or unsubstituted alkyl or aryl; and —W—$(CH_2)_t$—$NR_dR_e$, wherein t is an integer from about 1 to about 6; W is a direct bond, O, S, S(O), $S(O)_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together form a five- or six-membered heterocyclic ring.

Preferably $R_a$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted and unsubstituted tetrazolyl, substituted and usubstituted styryl, substituted and unsubstituted arylthio, substituted and unsubstituted heteroarylthio; $CH_2OR_c$, wherein $R_c$ is hydrogen or substituted or unsubstituted alkyl or aryl; and —W—$(CH_2)_t$—$NR_dR_e$, wherein t is an integer from about 1 to about 6; W is a direct bond, O, S, S(O), $S(O)_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together form a five- or six-membered heterocyclic ring.

In one embodiment, $R_2$ is an oxacycloalkyl group of the formula

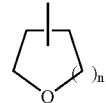

wherein n is 1, 2 or 3.

In another embodiment, $R_2$ is of the formula

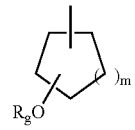

where m is 0, 1, 2 or 3 and $R_g$ is H or —$(CH_2)_pN(R_4)R_5$, where p is an integer from about 2 to about 6. $R_4$ and $R_5$ are each, independently, H, azabicycloalkyl or Y-Z, wherein Y is selected from the group consisting of —C(O)—, —$(CH_2)_n$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group or $R_4$, $R_5$, and the nitrogen atom together form a 3, 4, 5, 6 or 7-membered, substituted or unsubstituted heterocyclic or heterobicyclic group.

In another embodiment, $R_2$ is of the formula

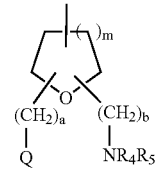

wherein m is 1, 2 or 3. a and b ar each, independently, an integer from 0 to about, except that when the two substituents are attached to the same carbon atom, a is from 1 to about 6. Q is $NR_4R_5$, or —$OR_6$. Each $R_4$ and $R_5$ is, independently, H, azabicycloalkyl or Y-Z, wherein Y is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; where p is an integer from 0 to about 6, q is an integer from 0 to about 6, and r is 0, 1 or 2; and Z is a substituted or unsubstituted alkyl, amino, aryl, heteroaryl or heterocycloalkyl group. $R_4$, $R_5$ and the nitrogen atom can also together form a 3, 4, 5, 6 or 7-membered, substituted or unsubstituted heterocyclic or heterobicyclic group.

In another embodiment, $R_2$ is of the formula

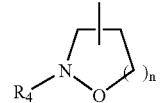

where n is 1, 2 or 3; and $R_4$ is H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In another embodiment, $R_2$ is of the formula

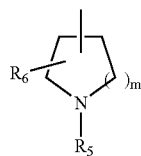

where m is 0, 1, 2 or 3. $R_5$ is H, azabicycloalkyl or Y-Z, where Y is selected from the group consisting of —C(O)—, —(CH$_2$)$_p$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; where p is an integer from 0 to about 6, q is an integer from 0 to about 6, and r is 0, 1 or 2; and Z is a substituted or unsubstituted alkyl, amino, aryl, heteroaryl or heterocycloalkyl group. $R_6$ represents one or more substituents independently selected from the group consisting of hydrogen, hydroxy, oxo and substituted or unsubstituted alkyl, aryl, heteroaryl, alkoxycarbonyl, alkoxyalkyl, aminocarbonyl, alkylcarbonyl, arylcarbonyl, heteroarylcarbonyl, aminoalkyl and arylalkyl groups, provided that the carbon atoms adjacent to the nitrogen atom are not substituted by a hydroxy group.

In another embodiment, $R_2$ is of the formula

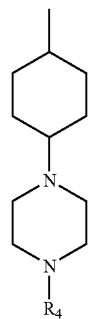

wherein $R_4$ is H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In another embodiment, $R_2$ is of the formula

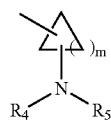

where m is an integer from 1 to about 6; and $R_4$ and $R_5$ are each, independently, H, azabicycloalkyl or Y-Z, wherein Y is selected from the group consisting of —C(O)—, (CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_4$, $R_5$ and the nitrogen atom can also together form a 3, 4, 5, 6 or 7-membered, substituted or unsubstituted heterocyclic or heterobicyclic group.

In another embodiment, $R_2$ is of the formula

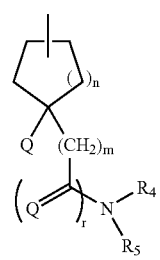

where n is an integer from 0 to about 4; and r is 0 or 1. When r is 0, m is an integer from 0 to 6. When r is 1, m is an integer from 1 to 6. Q is —NR$_4$R$_5$ or —OR$_6$. Each $R_4$ and $R_5$ is, independently, H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_4$, $R_5$ and the nitrogen atom can also together form a 3, 4, 5 or 6-membered, substituted or unsubstituted heterocyclic group. $R_6$ is hydrogen or a substituted or unsubstituted alkyl group.

In another embodiment, $R_2$ is of the formula

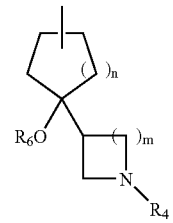

where n is an integer from 0 to about 4 and m is an integer from 0 to about 6. $R_4$ is H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_6$ is hydrogen or a substituted or unsubstituted alkyl group.

In embodiments of $R_2$ described above which include an —N(R$_4$)R$_5$ group, this group can form a heterocyclic group of the formula

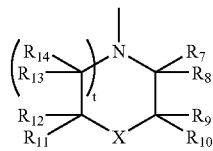

where $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, $CONHR_{15}$, $COOR_{15}$, $CH_2OR_{15}$ or $CH_2NR_{15}(R_{16})$, where $R_{15}$ and $R_{16}$ are each, independently, H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group; or $R_{15}$, $R_{16}$ and the nitrogen atom together form a 3, 4, 5, 6 or 7-membered, substituted or unsubstituted heterocyclic or heterobicyclic group; X is O, S, SO, SO$_2$, CH$_2$, CHOR$_{17}$ or NR$_{17}$, wherein $R_{17}$ is hydrogen, substituted or unsubstituted alkyl, aryl, arylalkyl, —C(NH)NH$_2$, —C(O)R$_{17}$, or —C(O)OR$_{18}$, wherein $R_{18}$ is hydrogen, substituted or unsubstituted alkyl, aryl or arylalkyl; and t is 0 or 1.

$R_4$, $R_5$ and the nitrogen atom can also together form a heterocyclic group of the formula

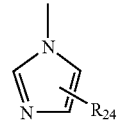

where $R_{19}$ and $R_{20}$ are each, independently, hydrogen or lower alkyl; or $R_{19}$ and $R_{20}$ together are an oxygen atom. $R_{21}$, and $R_{22}$ are each, independently, H azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_{21}$, $R_{22}$ and the nitrogen atom can also together form a 3, 4, 5 or 6-membered, substituted or unsubstituted heterocyclic group. m is an integer from 1 to about 6; and n is an integer from 0 to about 6.

$R_4$, $R_5$ and the nitrogen atom can also together form a heterocyclic group of the formula

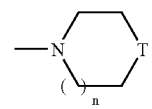

where m is an integer from 1 to 6. $R_{23}$ is CH$_2$OH, NRR', C(O)NR'R or COOR, where R and R' are each independently hydrogen or a substituted or unsubstituted alkyl, aryl or arylalkyl group.

$R_4$, $R_5$ and the nitrogen atom can also together form a heterocyclic group of the formula

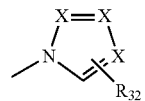

where $R_{24}$ is a substituted or unsubstituted alkyl, aryl or arylalkyl group, carboxyl, cyano, C(O)OR$_{25}$, CH$_2$OR$_{25}$, CH$_2$NR$_{26}$R$_{27}$ or C(O)NHR$_{26}$. $R_{25}$ is a substituted or unsubstituted alkyl, aryl, arylalkyl, heterocyclic or heteroaryl group. $R_{26}$ and $R_{27}$ are each, independently, H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_{26}$, $R_{27}$ and the nitrogen atom can also together form a 3, 4, 5 or 6-membered, substituted or unsubstituted heterocyclic group.

In one subset of compounds of Formulas 1–109, at least one of $R_4$ and $R_5$ is of the formula Y-Z, where Z is of the formula where T is C(O), S, SO, SO$_2$, CHOR or NR, wherein R is hydrogen or a substituted or unsubstituted alkyl, aryl or arylalkyl group; and n is 0, 1 or 2.

In another embodiment, at least one of $R_4$ and $R_5$ is of the formula Y-Z, where Z is —N(R$_{28}$)R$_{29}$, and $R_{28}$, and $R_{29}$ are each, independently, substituted or unsubstituted carboxyalkyl, alkoxycarbonylalkyl, hydroxyalkyl, alkylsulfonyl, alkylcarbonyl or cyanoalkyl. $R_{28}$ and $R_{29}$, together with the nitrogen atom, can also form a five- or six-membered heterocyclic group.

In yet another embodiment, at least one of $R_4$ and $R_5$ is of the formula Y-Z, where Z is of the formula N(R$_{30}$)R$_{31}$. $R_{30}$ and $R_{31}$, are each, independently, hydrogen, alkyl, alkoxycarbonyl, alkoxyalkyl, hydroxyalkyl, aminocarbonyl, cyano, alkylcarbonyl or arylalkyl.

In another embodiment, at least one of $R_4$ and $R_5$ is Y-Z, where Z is of the formula Each X is, independently, CH or N. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y-Z where Z is of the formula

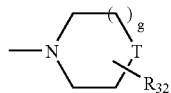

where g is 0 or 1; and T is C(O), O, S, SO, $SO_2$, $CH_2$, $CHOR_{17}$ or $NR_{17}$. $R_{17}$ is hydrogen, substituted or unsubstituted alkyl, aryl, arylalkyl, —C(NH)NH$_2$, —C(O)R$_{18}$, C(O)NH$_2$ or —C(O)OR$_{18}$, where $R_{18}$ is hydrogen, substituted or unsubstituted alkyl, aryl or arylalkyl. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y-Z, where Z is of the formula

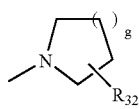

where g is 0, 1 or 2; and $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

Z can also be of the formula

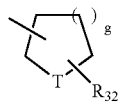

where g is 0, 1, 2 or 3, and T is O, S, SO, $SO_2$, $CH_2$, $CHOR_{17}$ or $NR_{17}$. $R_{17}$ is hydrogen, substituted or unsubstituted alkyl, aryl, arylalkyl, —C(NH)NH$_2$, —C(O)R$_{17}$, or —C(O)OR$_{18}$, wherein $R_{18}$ is hydrogen, substituted or unsubstituted alkyl, aryl or arylalkyl. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y-Z, wherein Z is of the formula

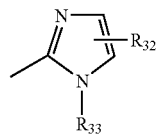

Where $R_{32}$ is hydrogen, cyano or substituted or unsubstituted alkyl, alkoxycarbonyl, alkoxyalkyl, hydroxyalkyl, aminocarbonyl, alkylcarbonyl, thioalkoxy or arylalkyl; and $R_{33}$ is hydrogen or substituted or unsubstituted alkyl, alkoxycarbonyl, alkoxyalkyl, aminocarbonyl, perhaloalkyl, alkenyl, alkylcarbonyl or arylalkyl.

In another subset of the compounds of Formulas 1–109, $R_2$ is of the formula

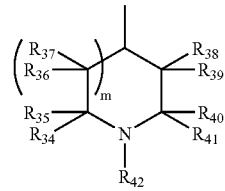

where m is 0 or 1; $R_{34}$, $R_{35}$, $R_{36}$, $R_{37}$, $R_{38}$, $R_{39}$, $R_{40}$ and $R_{41}$ are each, independently, methyl or hydrogen; or at least one pair of substituents $R_{34}$ and $R_{35}$; $R_{36}$ and $R_{37}$; $R_{38}$ and $R_{39}$; or $R_{40}$ and $R_{41}$ together are an oxygen atom. $R_{42}$ is H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In a preferred embodiment, $R_{42}$ is of the formula

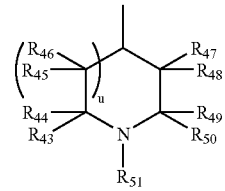

Where u is 0 or 1; $R_{43}$, $R_{44}$, $R_{45}$, $R_{46}$, $R_{47}$, $R_{48}$, $R_{49}$ and $R_{50}$ are each, independently, methyl or hydrogen; or at least one pair of substituents $R_{43}$ and $R_{44}$; $R_{45}$ and $R_{46}$; $R_{47}$ and $R_{48}$; or $R_{49}$ and $R_{50}$ together are an oxygen atom. $R_{51}$ is H, azabicycloalkyl or V-L, where V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and L is a substituted or unsubstituted alkyl, amino, aryl, heteroaryl or heterocycloalkyl group.

In another subset of the compounds of Formulas 1–109, $R_2$ is of the formula

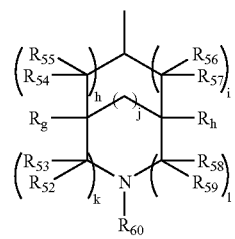

Where h, i, j, k and l are independently 0 or 1; $R_{52}$, $R_{53}$, $R_{54}$, $R_{55}$, $R_{56}$, $R_{57}$, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom. $R_{60}$ is H, azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. In one embodiment, $R_{60}$ is of the formula

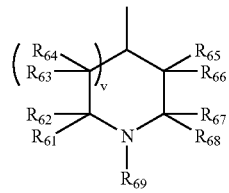

Where v is 0 or 1; $R_{61}$, $R_{62}$, $R_{63}$, $R_{64}$, $R_{65}$, $R_{66}$, $R_{67}$ and $R_{68}$ are each, independently, lower alkyl or hydrogen; or at least one pair of substituents $R_{61}$, and $R_{62}$; $R_{63}$ and $R_{64}$; $R_{65}$ and $R_{66}$; and $R_{67}$ and $R_{68}$ together are an oxygen atom; and $R_{69}$ is H, azabicycloalkyl or V-L, where V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and L is a substituted or unsubstituted alkyl, amino, aryl, heteroaryl or heterocycloalkyl group.

In another subset of compounds of Formula (I), $R_3$ is H; $R_2$ is -$Z^{101}$-$Z^{102}$ where $Z^{101}$ is a covalent bond, —(C$_1$–C$_6$)—, —(C$_1$–C$_6$)—O—, —(C$_1$–C$_6$)—C(O)—, —(C$_1$–C$_6$)—C(O)O—, —(C$_1$–C$_6$)—C(O)—NH—, —(C$_1$–C$_6$)—C(O)—N((C$_1$–C$_6$))— or a substituted phenyl group; and $Z^{102}$ is hydrogen, a substituted or unsubstituted alkyl group or a substituted or unsubstituted, saturated or unsaturated heterocyclic group.

In another subset of compounds of Formula (I) $Z^{101}$ is selected from the group consisting of —CH$_2$—C(O)O—, —CH$_2$—C(O)—, —CH$_2$—C(O)—NH—, —CH$_2$—C(O)—N(Me)—, —CH(Me)—C(O)O—, —(CH$_2$)$_3$—C(O)O—, —CH(Me)—C(O)—NH—, and —(CH$_2$)$_3$—C(O)—NH—;

$Z^{102}$ is selected from the group consisting of hydrogen, methyl, ethyl, N,N-dimethylaminoethyl, N,N-diethylaminoethyl, 2-phenyl-2-hydroxyethyl, morpholino, piperazinyl, N-methylpiperazinyl and 2-hydroxymethylpyrrolidinyl.

In another subset of compounds of Formula (I), $R_1$ is

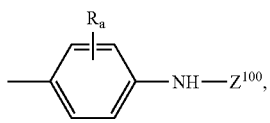

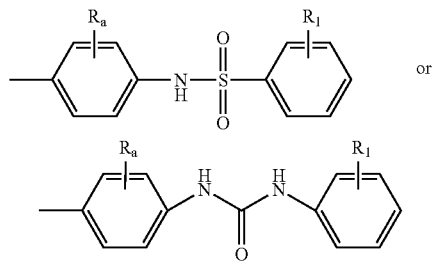

where $Z^{100}$ is a substituted or unsubstituted benzoxazolyl or a substituted or unsubstituted benzthiazolyl.

In another subset of compounds of Formula (I), $R_1$ is

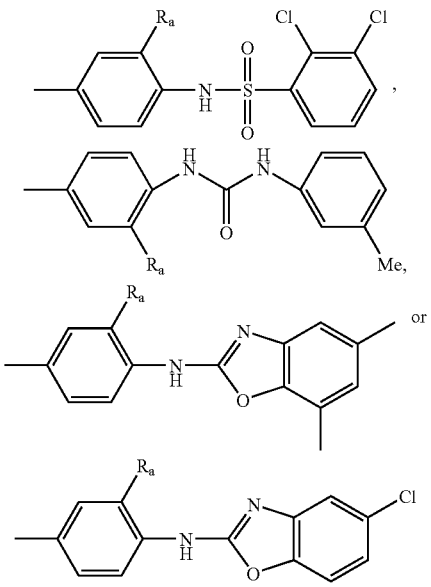

where there is only one $R_a$ and it is H or F.

In another subset of compounds of Formula (I) $Z^{101}$ is a covalent bond; and $Z^{102}$ is an optionally substituted pyridyl.

In another subset of compounds of Formula (I), $R_1$ is

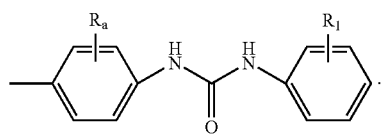

In another subset of compounds of Formula (I), $R_3$ is H; $R_2$ is cyclopentyl; and

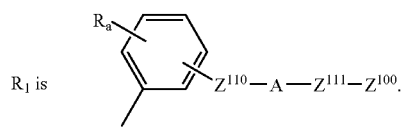

In another subset of compounds of Formula (I), $Z^{110}$ is hydrogen; A is O; and $Z^{100}$ is optionally substituted phenyl, furanyl or thienyl, where $Z^{100}$ is optionally substituted with one or more substituents each independently selected from the group consisting of F, COOH, $NO_2$, OMe, —COOMe, $OCF_3$ and $CF_3$.

In another subset of compounds of Formula (I), $Z^{110}$ is hydrogen;

A is —O—, —O—$(CR_2)_n$—C(O)— or —O—$(CR_2)_n$—O—;

n for each occurrence is 0 to 3;

$Z^{100}$ is an optionally substituted group selected from the group consisting of cyclohexyl, phenyl, tetrahydropyranyl, tetrahydrofuranyl, isoxazolyl and piperidinyl; where $Z^{100}$ is optionally substituted with one or more substituents selected from the group consisting of alkyl, alkoxy, halo, hydroxy and alkoxycarbonyl.

In another subset of compounds of Formula (I), $R^2$ is an optionally substituted group selected from the group consisting of cyclobutyl and cyclohexyl.

In another subset of compounds of Formula (I), $R^2$ is optionally substituted with one or more substituents selected from the group consisting of hydroxy, alkyl, hydroxyalkyl, carboxyalkyl and phenylalkoxyalkyl.

In another subset of compounds of Formula (I), $R_1$ is 4-phenoxyphenyl.

In another subset of compounds of Formula (I), m is 2; a is 0; $R_6$ is H; b is 1 or 2; and $R_4$ and $R_5$ are each hydrogen.

In another subset of compounds of Formula (I), m is 0, 1 or 2; $R_6$ is hydrogen; $R_5$ is H or Y-Z;
  where Y is a covalent bond, —C(O)—, —$(CH_2)_q$O—, —$(CH_2)_q$—, —$(CH_2)_q$C(O)— or —C(O)$(CH_2)_q$—, where the alkyl portion of —$(CH_2)_q$O—, —$(CH_2)_p$—, —$(CH_2)_q$C(O)— and —C(O)$(CH_2)_q$— is optionally substituted by a halogen, hydroxy or an alkyl group; and
  Z is hydrogen, alkyl, optionally substituted alkyl, alkoxyalkyl, optionally substituted heterocycloalkyl, optionally substituted heteroaryl, or optionally substituted amino.

In another subset of compounds of Formula (I), Z is hydrogen, methyl, ethyl, hydroxymethyl, methoxyethyl, N-methyl-piperidinyl, (t-butoxycarbonyl)(hydroxy)-piperidinyl, hydroxypiperidinyl, (hydroxymethyl)piperdinyl, (hydroxy)(methyl)-piperidinyl, morpholino, (methoxyethyl) piperizinyl, methylpiperizinyl, 4-piperidinylpiperidinyl, imidazolyl, methylimidazolyl, N-methylamino, N,N-dimethylamino, N-isopropylamino, N,N-diethylamino, 2,3-dihydroxypropylamino, 2-hydroxyethylamino, 3-hydroxypropylamino, methoxyethylamino, ethoxycarbonylmethylamino, phenylmethylamino, N-methyl-N-methoxyamino,

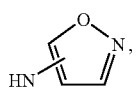

furanylmethylamino, piperidinylethylamino, N-(2-N,N-dimethylaminoethyl)-N-methylamino, 2-N,N-dimethylaminoethylamino, N-methyl-N-(N-methylpiperidin-4-yl)amino, 2-morpholino-ethylamino, 3-morpholino-propylamino, 3-imidazolylpropylamino, or 3-(2-oxopyrrolidinyl)propylamino.

In another subset of compounds of Formula (I), m is 2; $R_5$ is Y-Z; Y is —C(O)—;

and Z is

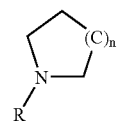

where n is 0, 1, 2 or 3.

In another subset of compounds of Formula (I), $R_4$ is hydrogen or methyl;

$R_1$ is

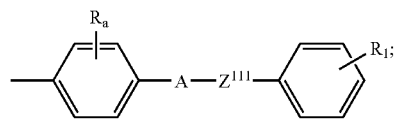

A is selected from the group consisting of O, —N(R)— and —N(R)C(O)—;

$Z^{111}$ is —$(CH_2)_n$-cycloalkyl-$(CH_2)_n$—;

R is hydrogen or alkyl;

n is 0 to 5;

$R_a$ is one or more substituents each independently selected from the group consisting of H, OH, F, Cl, methyl and methoxy; and $R_b$ is one or more substituents each independently selected from the group consisting of H, CN, F, $CF_3$, $OCF_3$, methyl, methoxy and an optionally substituted amino group;
  where said amino group is optionally substituted with one or two groups each independently selected from the group consisting of alkyl, alkoxyalkyl, phenyl, substituted phenyl, and optionally substituted heteroaryl.

In another subset of compounds of Formula (I), $R_b$ is 4-methylphenylthio or 2-pyridinylthio.

In another subset of compounds of Formula (I), $R_1$ is

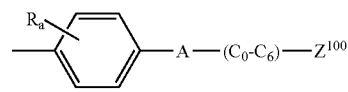

where $Z^{100}$ is selected from the group consisting of benzo[b]thiophene, furanyl and thiophene.

In another subset of compounds of Formula (I), wherein $R_a$ is alkoxy; A is —NH—C(O)—; and there is a covalent bond between A and $Z^{100}$.

In another subset of compounds of Formula (I), $R_1$ is

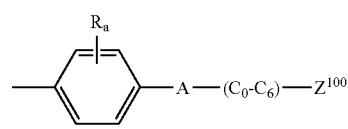

A is selected from the group consisting of —N(R)—C(O)—N(R)—, —(CH$_2$)$_n$—N(R)C(O)N(R)—, —N(R)— and —N(R)—SO$_2$—; R is hydrogen or alkyl;

Z$^{100}$ is

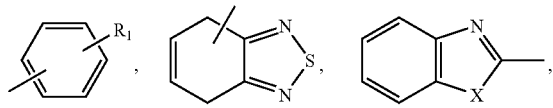

pyridinyl, thiazolyl, furanyl, benzofuranyl or oxazolyl;

X is S, O or NR where R for each occurrence is independently H or Me;

R$_a$ is one or more substituents each independently selected from the group consisting of H and F; and R$_b$ is one or more substituents each independently selected from the group consisting of H, F, Cl, Br, NO$_2$, CF$_3$, alkyl, alkoxy and alkoxycarbonyl.

In another subset of compounds of Formula (I), R$_4$ is methyl; m is 1, 2 or 3; R$_5$ is Y-Z, where Y is —C(O)O—, —C(O)— or —C(O)—(CH$_2$)$_p$—; and Z is aminoalkyl, N-alkylamino, N,N-dialkylamino or hydroxyalkylaminoalkyl.

In another subset of compounds of Formula (I), R$_4$ is methyl; R$_1$ is

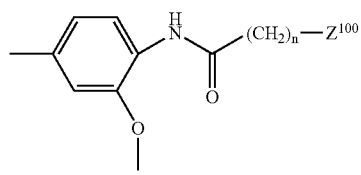

where n is 0 to 3; Z$^{100}$ is an optionally substituted group selected from the group consisting of indolyl, indenyl, methylindenyl, methylindolyl, dimethylaminophenyl, phenyl, cyclohexyl and benzofuranyl.

In another subset of compounds of Formula (I), R$_1$ is

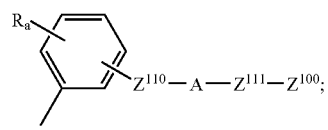

Z$^{100}$ is an optionally substituted group selected from the group consisting of phenyl, imidazolyl, indolyl, furanyl, benzofuranyl and 2,3-dihydrobenzofuranyl;

where Z$^{100}$ is optionally substituted with one or more substituents each independently selected from the group consisting of F, Cl, CN, optionally substituted alkyl, —O-(optionally substituted alkyl), —COOH, -Z$^{105}$-C(O)N(R)$_2$-Z$^{105}$-N(R)—C(O)-Z$^{200}$, -Z$^{105}$-N(R)—S(O)$_2$-Z$^{200}$, and -Z$^{105}$-N(R)—C(O)—N(R)-Z$^{200}$;

Z$^{105}$ is a covalent bond or (C$_1$–C$_6$);

Z$^{200}$ is an optionally substituted group selected from group consisting of (C$_1$–C$_6$), phenyl and —(C$_1$–C$_6$)-phenyl;

Z$^{110}$ and Z$^{111}$ are each independently a covalent bond or (C$_1$–C$_3$) group optionally substituted with alkyl, hydroxy, COOH, CN or phenyl; and A is O, —N(R)—C(O)—N(R)—, —N(R)—C(O)—O—, —N(R)— or —N(R)—C(O)—, where R is H or alkyl.

In another subset of compounds of Formula (I), R$_4$ is methyl.

In another subset of compounds of Formula (I), R$_1$ is

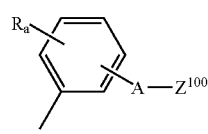

where Z$^{100}$ is an optionally substituted group selected from the group consisting of benzoxazolyl, benzothiazolyl and benzimidazolyl.

In another subset of compounds of Formula (I), R$_4$ is methyl; A is —NH—; there is only one R$_a$ and it is H or F; and Z$^{100}$ is optionally substituted with one or more substituents each independently selected from the group consisting of alkyl, halo, CF$_3$, and alkoxy.

In another subset of compounds of Formula (I), R$_1$ is

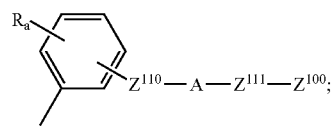

Z$^{100}$ is an optionally substituted group selected from the group consisting of phenyl, pyrrolyl, pyridyl, benzimidazolyl, naphthyl and

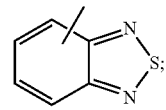

where Z$^{100}$ is optionally substituted with one or more substituents each independently selected from the group consisting of F, Cl, Br NO$_2$, amino, N-alkylamino, N,N-dialkylamino, CN, optionally substituted alkyl, —O— (optionally substituted alkyl) and phenyl;

Z$^{110}$ and Z$^{111}$ for each occurrence is independently (C$_0$–C$_3$) optionally substituted with optionally substituted phenyl; and A is —N(R)—C(O)—N(R)—, —N(R)—S(O)$_2$—, —N(R)—C(O)—, —N(R)— or —N(R)—C(O)—O—.

In another subset of compounds of Formula (I), R$_4$ is methyl and there is only one R$_a$ and it is F.

In another subset of compounds of Formula (I), $R_1$ is

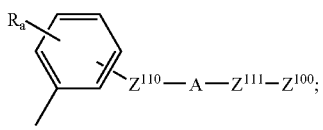

$Z^{100}$ is an optionally substituted group selected from the group consisting of phenyl, isoxazolyl, tetrahydronaphthyl, furanyl, benzofuranyl, pyridyl and indolyl;

where $Z^{100}$ is optionally substituted with one or more substituents each independently selected from the group consisting of F, CN, $NO_2$, —C(O)H, —$CONH_2$, —$NHSO_2CF_3$, optionally substituted alkyl, optionally substituted heteroaryl and —O-(optionally substituted alkyl);

$Z^{110}$ and $Z^{111}$ are each independently optionally substituted ($C_0$–$C_3$); and A is O, —N(R)—C(O)—($CH_2$)$_n$—N(R)—, —C(O)—N(R)—, —N(R)—C(O)—O—, —N(R)—C(O)— or —N(R)—.

In another subset of compounds of Formula (I), $R_4$ is methyl; $R_a$ is H or methoxy; and $Z^{110}$ and $Z^{111}$ are each unsubstituted.

In another subset of compounds of Formula (I), $R_1$ is

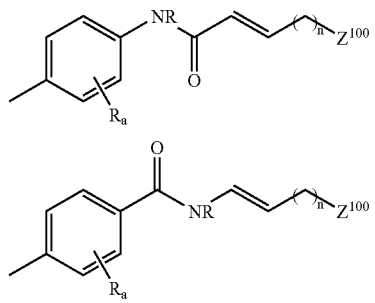

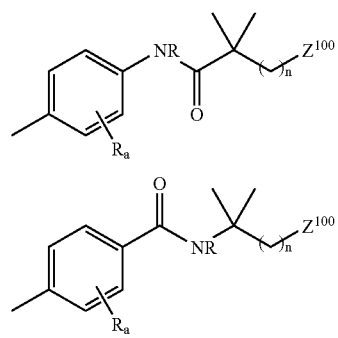

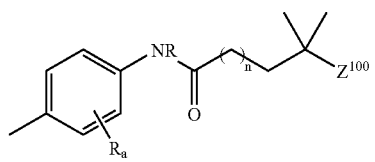

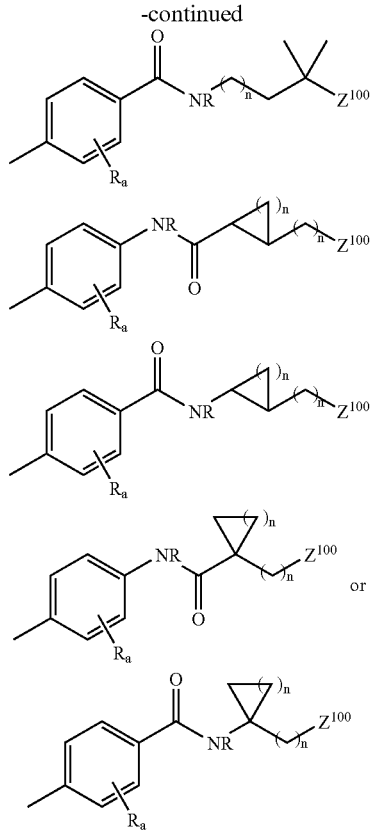

where R is H or lower alkyl and n is for each occurrence is independently 1 to 6.

In another subset of compounds of Formula (I), $R_1$ is

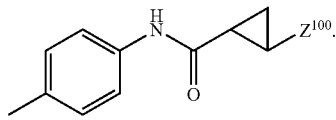

In another subset of compounds of Formula (I), $Z^{100}$ is substituted or unsubstituted phenyl.

In another subset of compounds of Formula (I), $R_1$ is

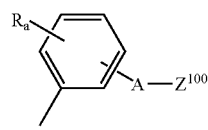

where $Z^{100}$ is an optionally substituted group selected from the group consisting of benzoxazolyl, benzothiazolyl and benzimidazolyl.

In another subset of compounds of Formula (I), n is 2; $R_6$ is H; m is 1; r is 1; and $R_4$ and $R_5$ are each hydrogen.

In another subset of compounds of Formula (I), $R_1$ is 4-phenoxyphenyl.

A subset of compounds of formulas 1–117 have $R_1$=4-phenoxyphenyl, $R_2$=cyclopentyl and both $R_3$=H. These compounds are illustrated below.

−37.70 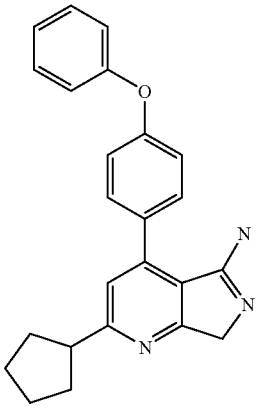
−35.74 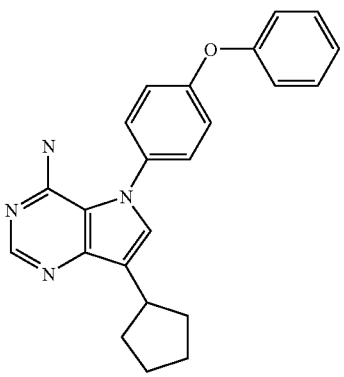
−35.04 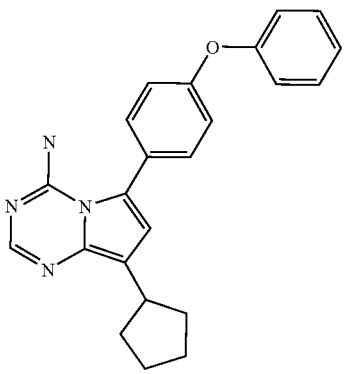
−34.22 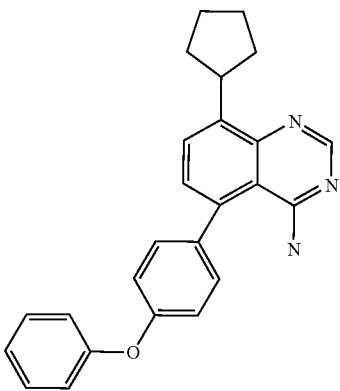
−37.84 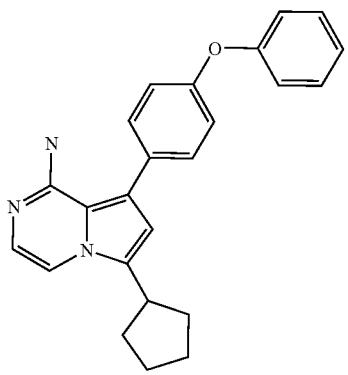
−36.16 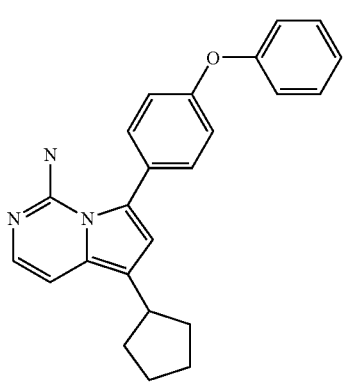
−38.61 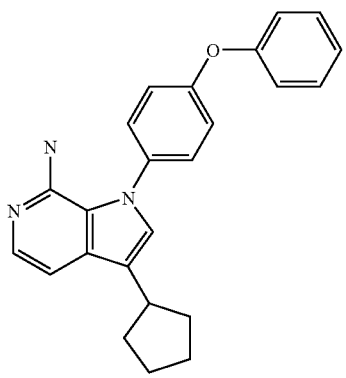
−35.42 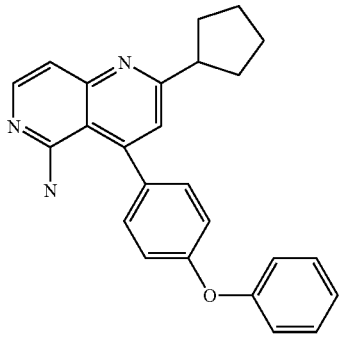

-30.16 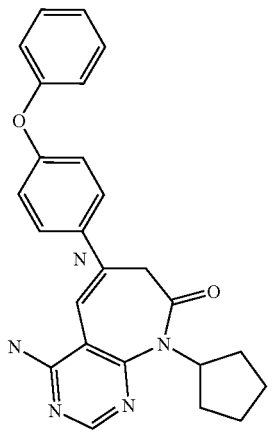
-37.77 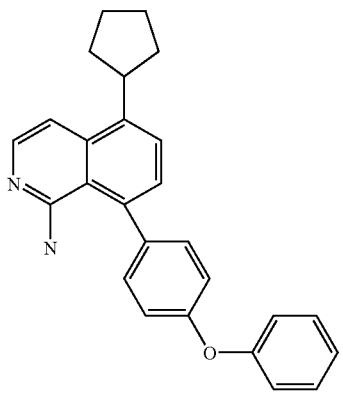
-33.60 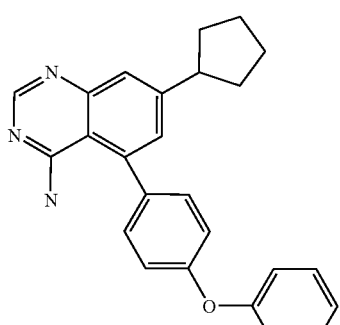
-36.33 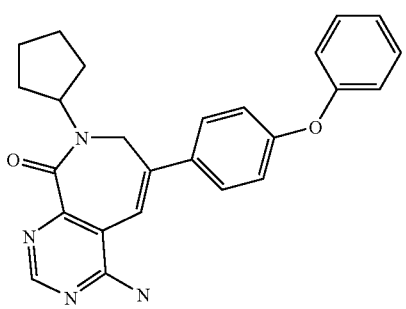
-33.02 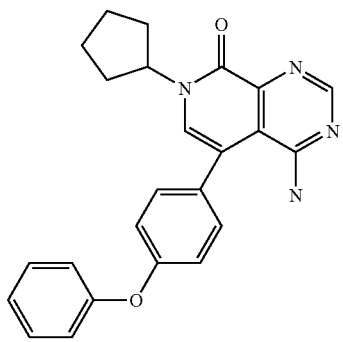
-35.11 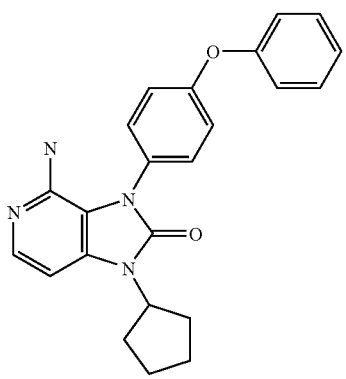
-33.20 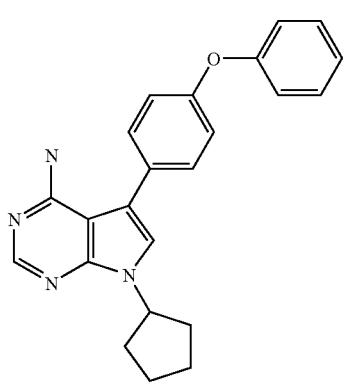
-40.20 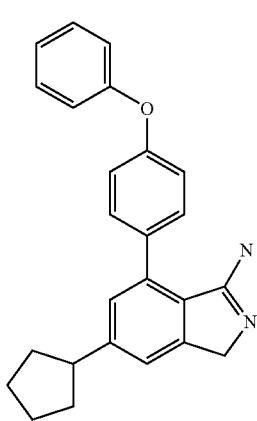

-37.05 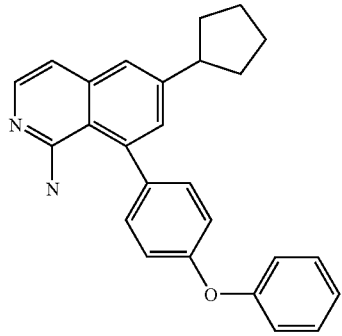
-37.83 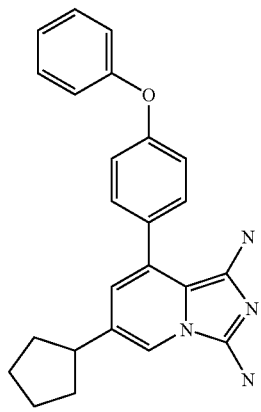
-32.93 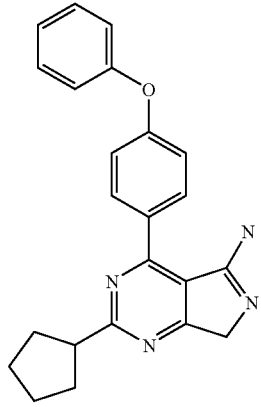
-31.46 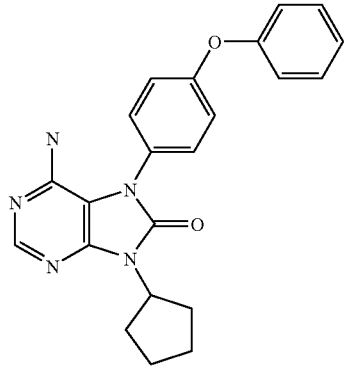
-31.32 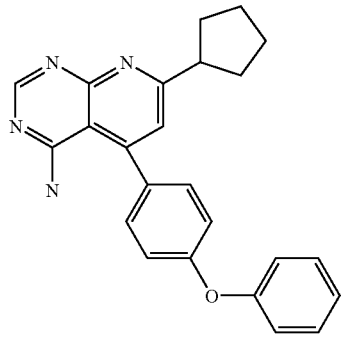
-32.12 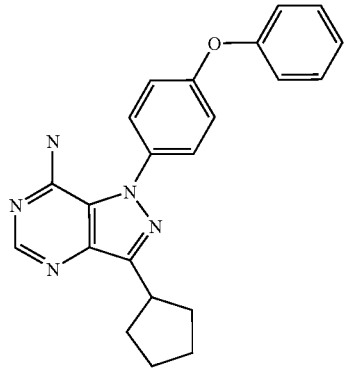
-36.54 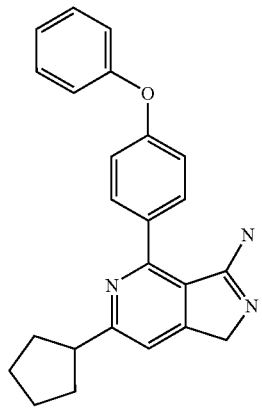
-36.11 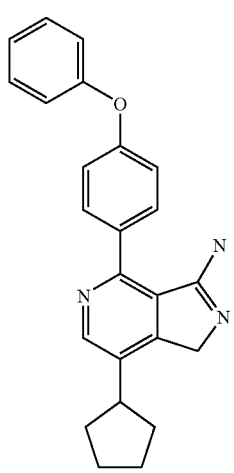

-continued
−32.39 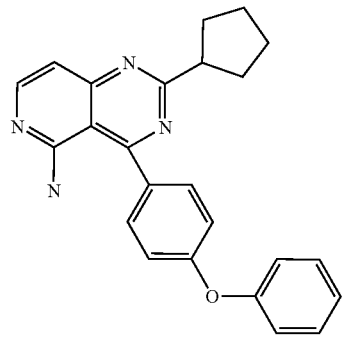
−31.81 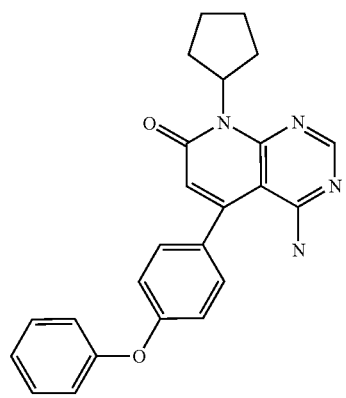
−35.08 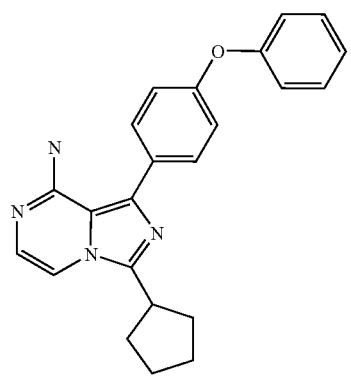
−35.14 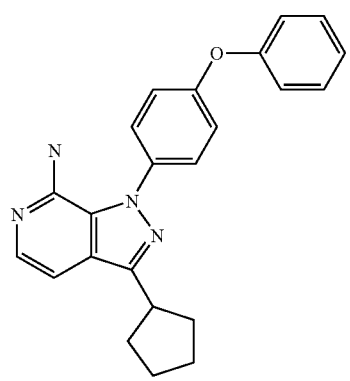
-continued
−31.67 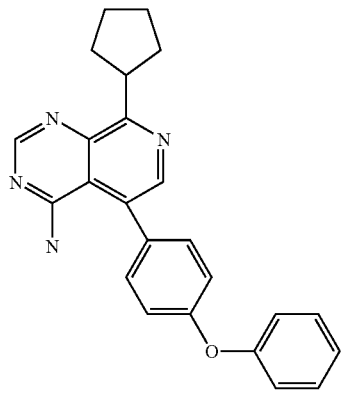
−30.27 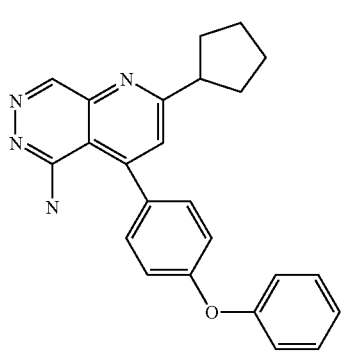
−33.20 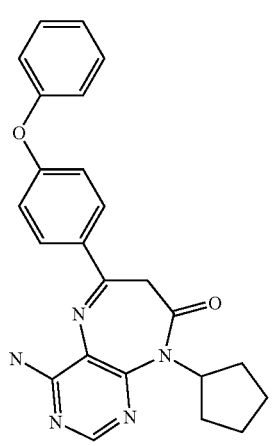
−33.36 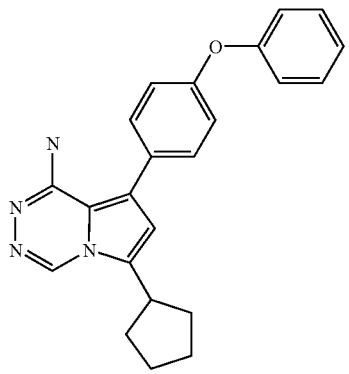

-continued
−31.05 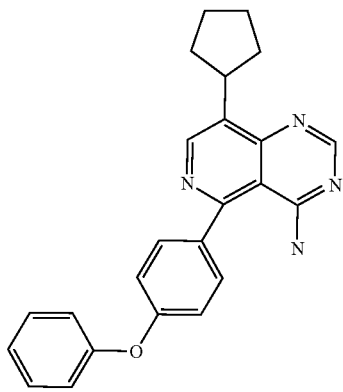
−30.85 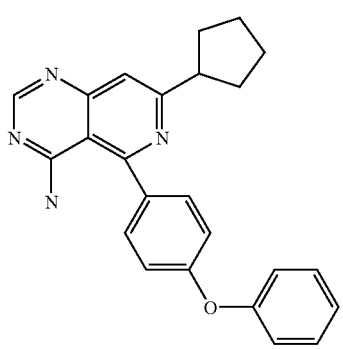
−33.15 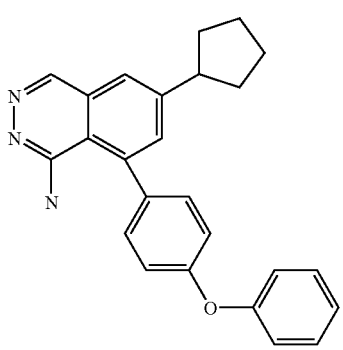
−36.69 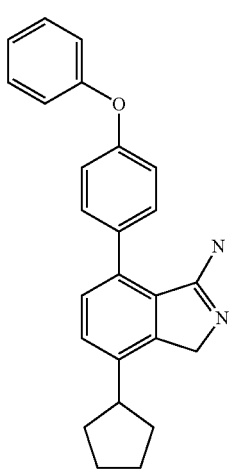
-continued
−31.66 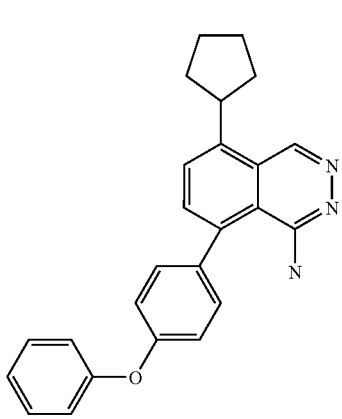
−31.20 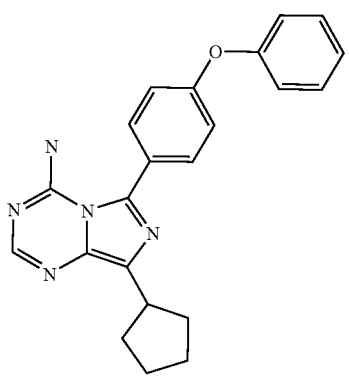
−36.25 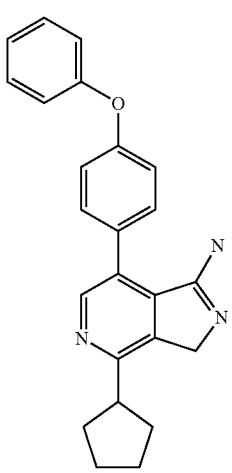
−34.81 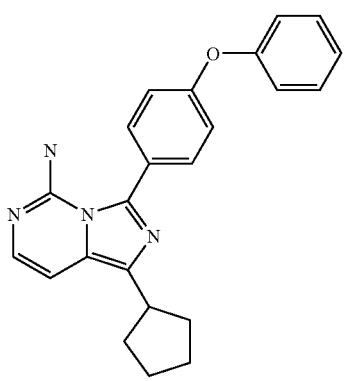

-continued
−34.44
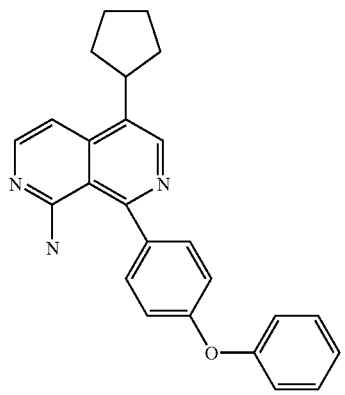
−34.95
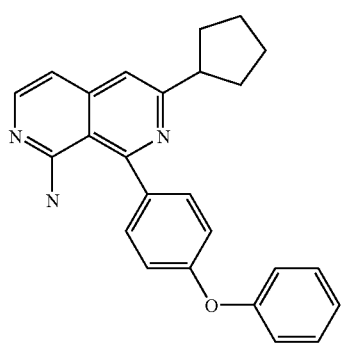
−31.33
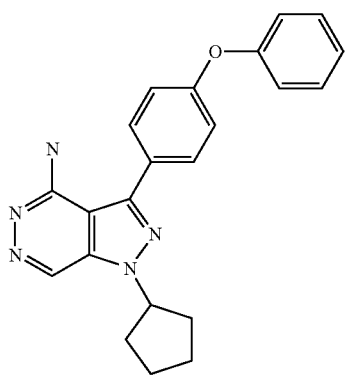
−28.20
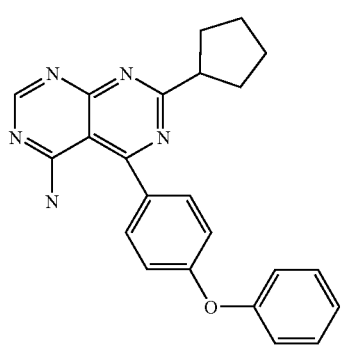
-continued
−33.92
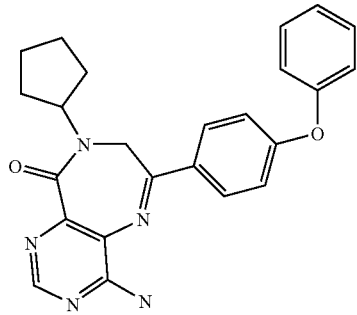
−34.81
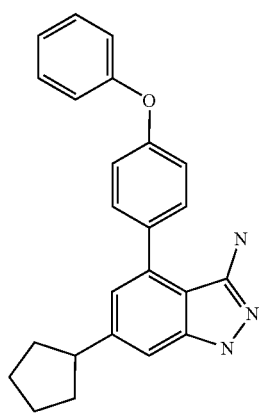
−31.62
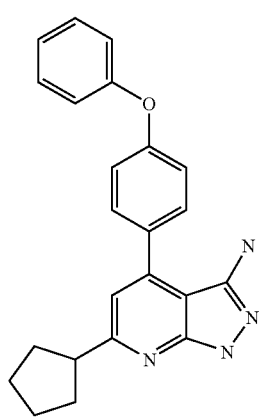
−29.33
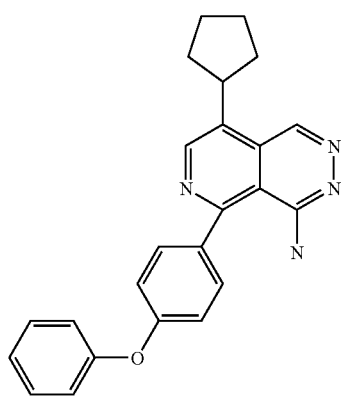

-30.84 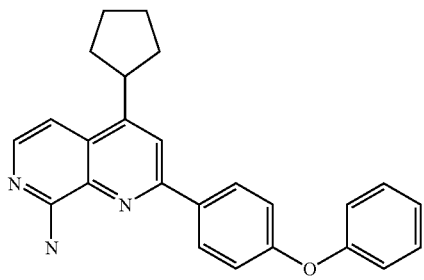
-29.87 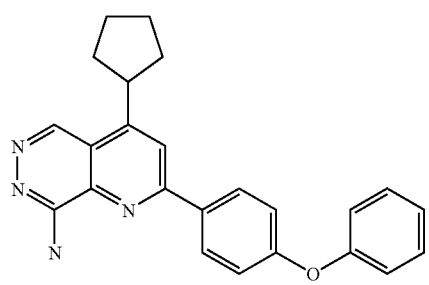
-33.01 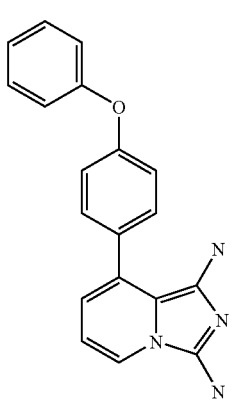
-26.77 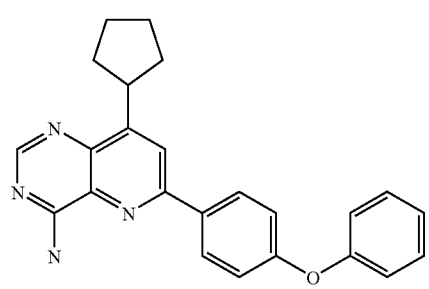
-29.05 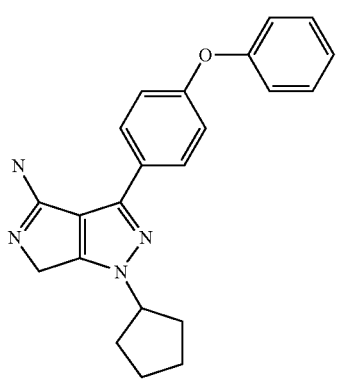
-31.45 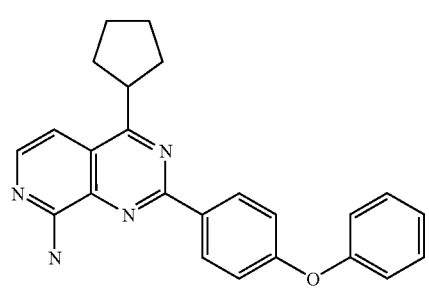
-25.70 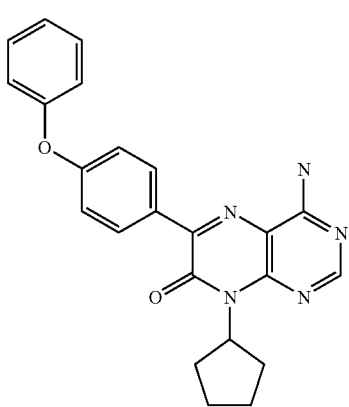
-28.04 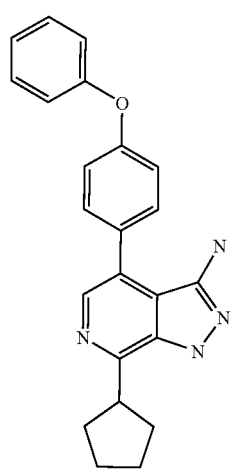

-continued
−24.41 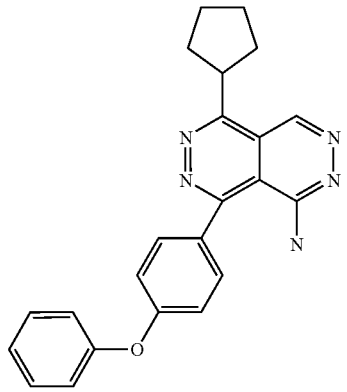
−26.81 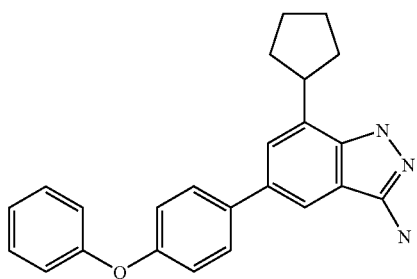
−29.50 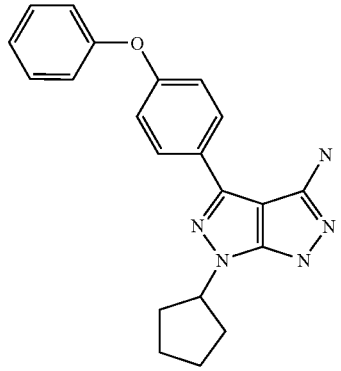
−25.41 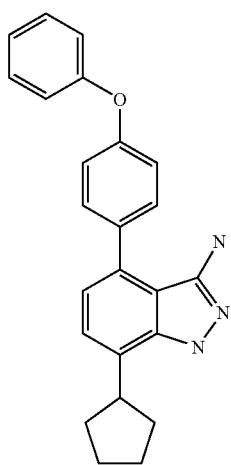
-continued
−30.56 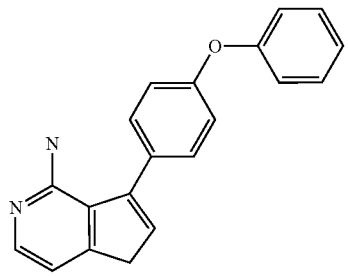
−30.32 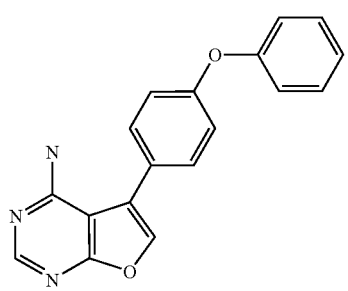
−28.75 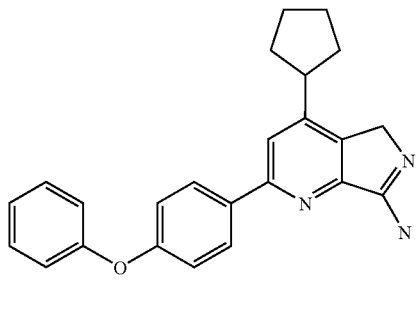
−25.61 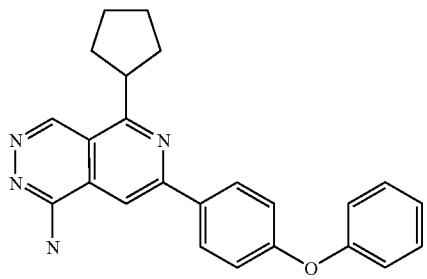
−24.08 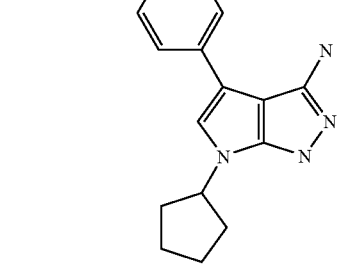

-continued
−29.48 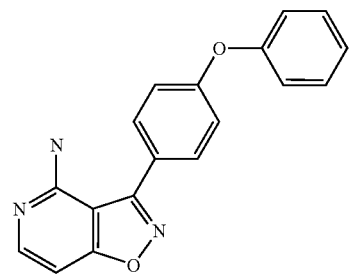
−25.01 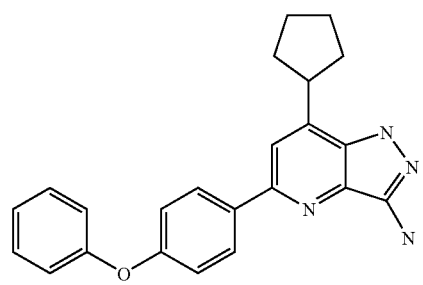
−27.51 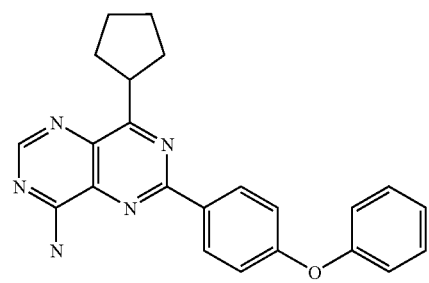
−27.71 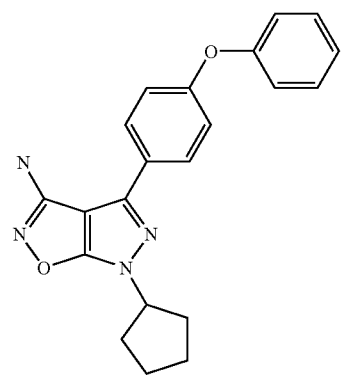
−27.20 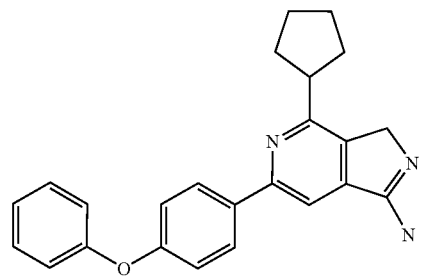
-continued
−25.19 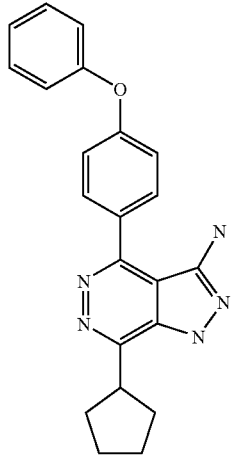
−27.85 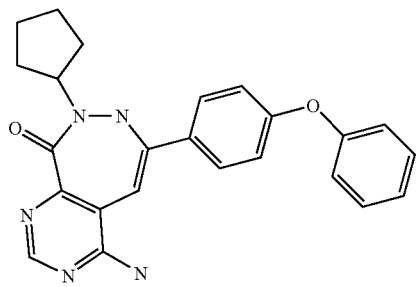
−32.71 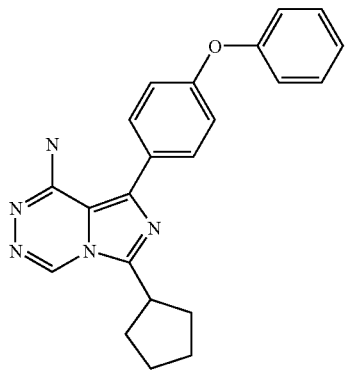
−28.25 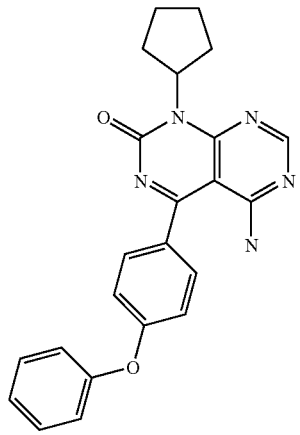

-continued
−32.98
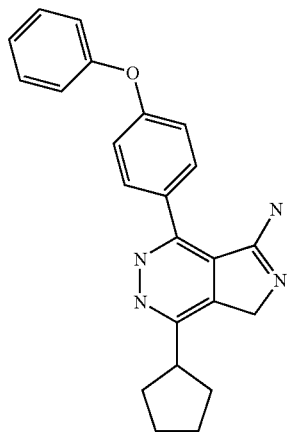
−29.79
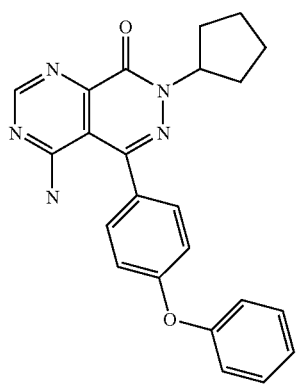
−27.09
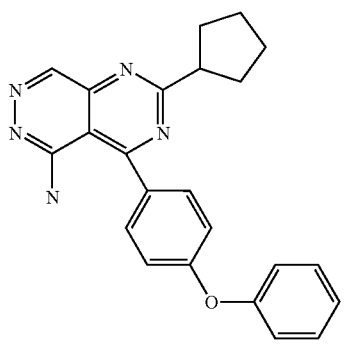
−28.63
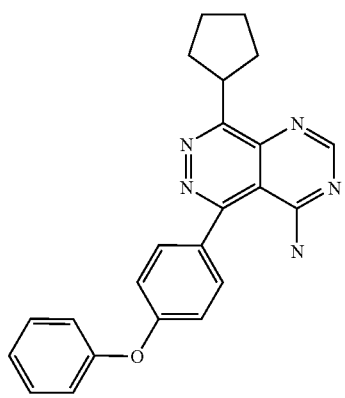
-continued
−29.15
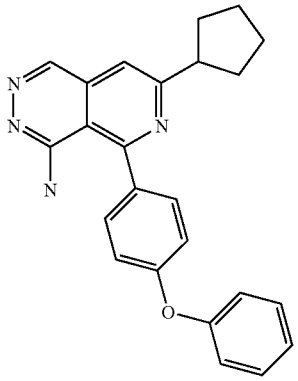
−32.03
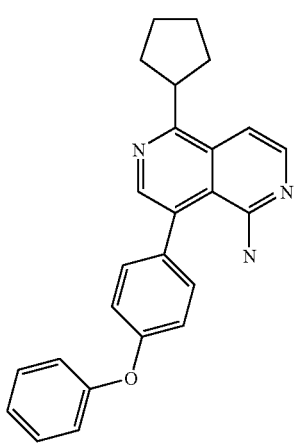
−29.93
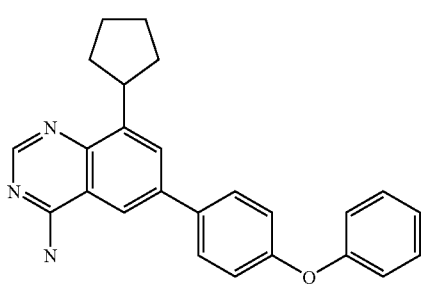
−32.33
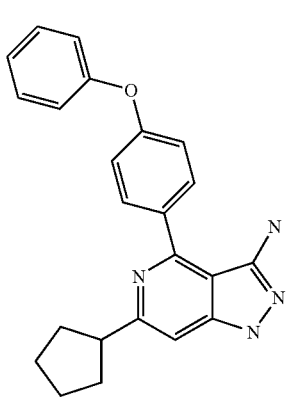

-continued
−34.13 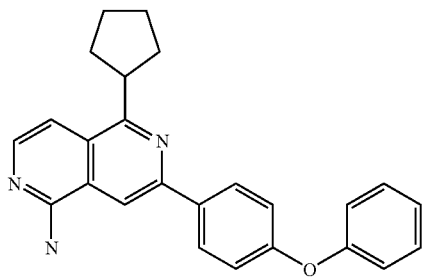
−28.49 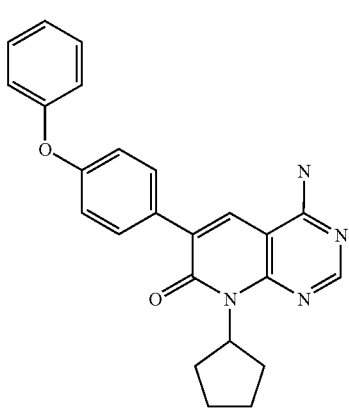
−32.77 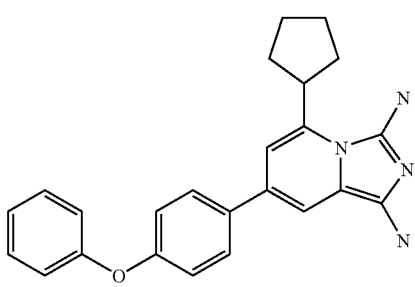
−31.73 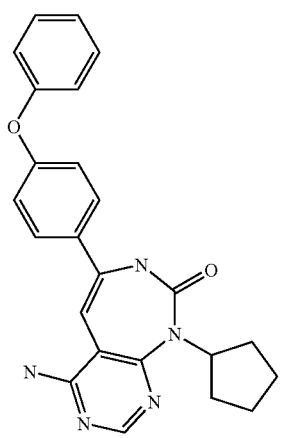
-continued
−33.16 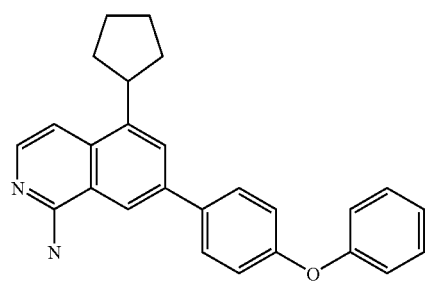
−28.17 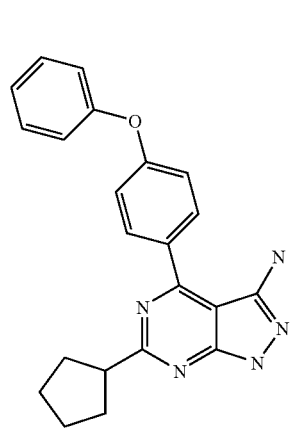
−26.47 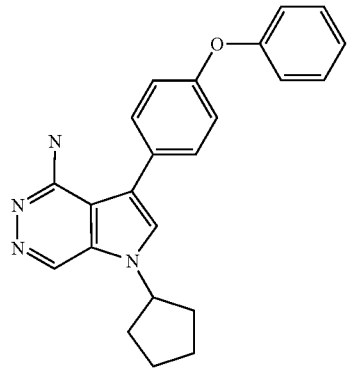
−30.35 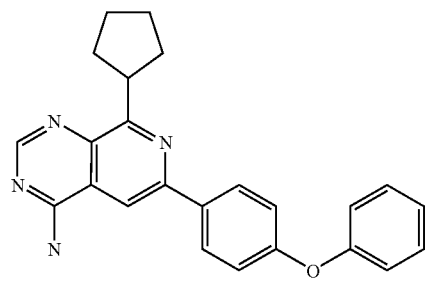

-continued
−26.83 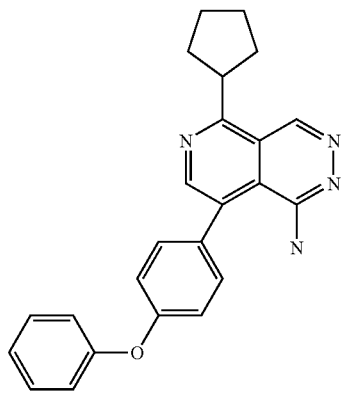
−31.73 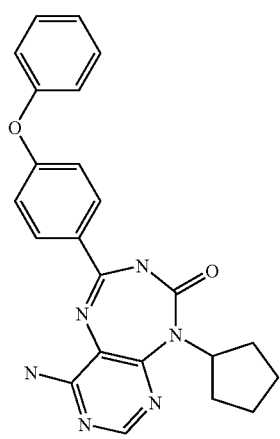
−29.09 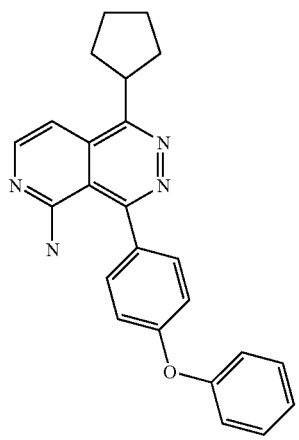
−33.70 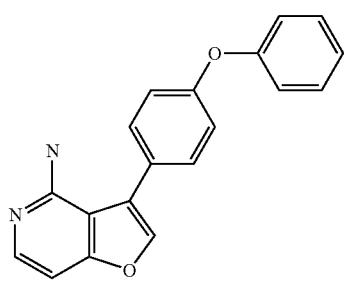
-continued
−31.83 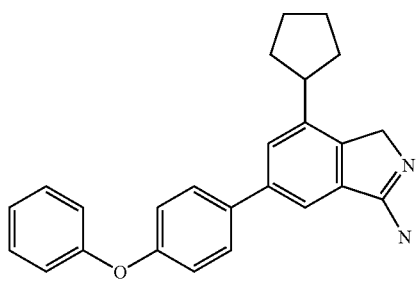
−28.62 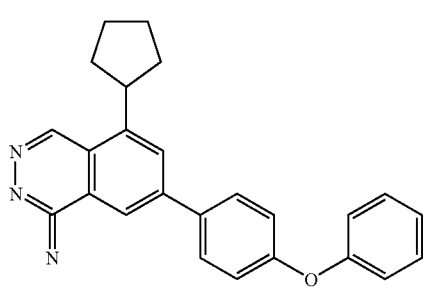
−22.15 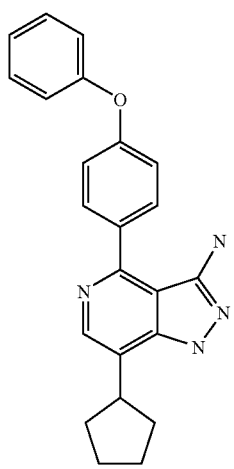
−25.89 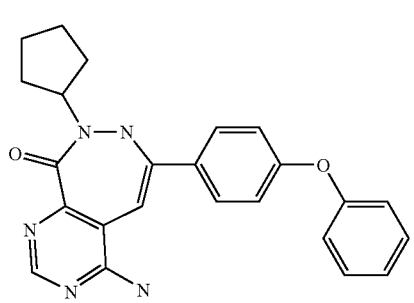

-continued
−23.04
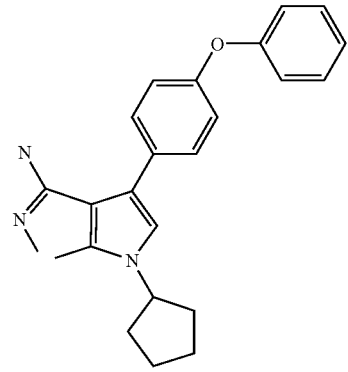
−25.48
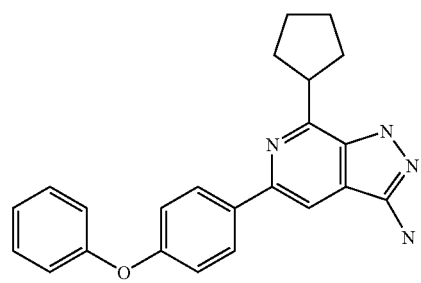
−27.65
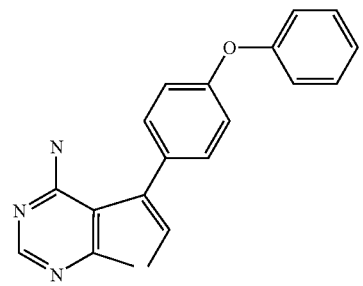
−24.20
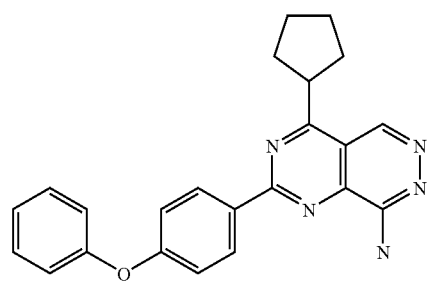
−27.48
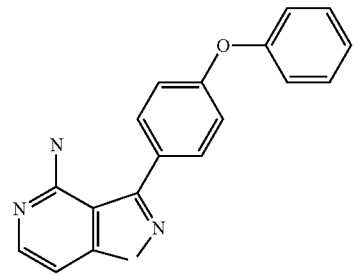
-continued
−27.35
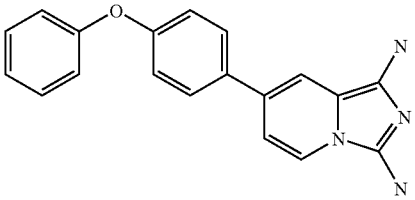
−25.22
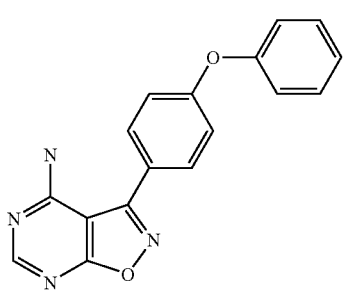
−24.07
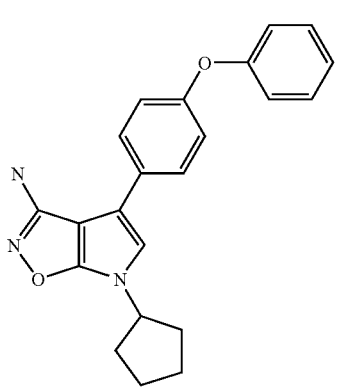
−24.82
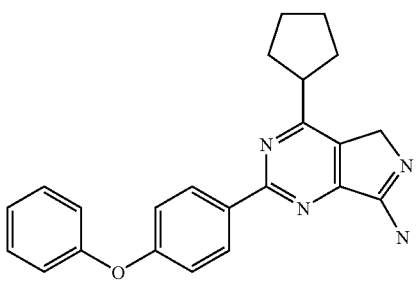
−24.42
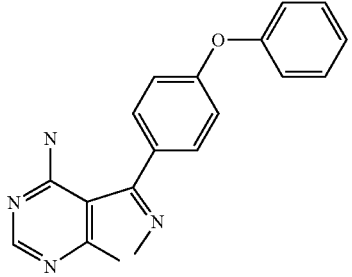

-22.00

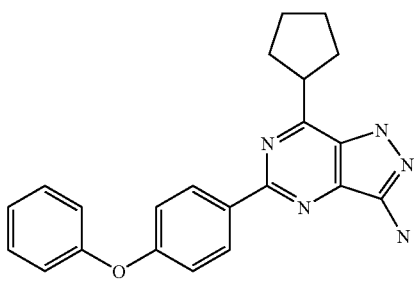

Compounds of formulas 1–109 may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of formulas 1–109 which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formulas 1–109 and their salts may exist in more than one crystal form and the present invention includes each crystal form and mixtures thereof.

Certain compounds of formulas 1–109 and their salts may also exist in the form of solvates, for example hydrates, and the present invention includes each solvate and mixtures thereof.

Certain compounds of formulas 1–109 may contain one or more chiral centres, and exist in different optically active forms. When compounds of formulas 1–109 contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formulas 1–109 contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formulas 1–109 and mixtures thereof.

Certain compounds of formulas 1–109 may exist in different tautomeric forms or as different geometric isomers, and the present invention includes each tautomer and/or geometric isomer of compounds of formulas 1–109 and mixtures thereof.

Certain compounds of formulas 1–109 may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formulas 1–109 and mixtures thereof.

Certain compounds of formulas 1–109 may exist in zwitterionic form and the present invention includes each zwitterionic form of compounds of formulas 1–109 and mixtures thereof. Heteroaromatic groups, as used herein, include heteroaryl ring systems (e.g., for purposes of exemplification, which should not be construed as limiting the scope of this invention: thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isothiazoles, oxazolyl or tetrazoles) and heteroaryl ring systems in which a carbocyclic aromatic ring, carbocyclic non-aromatic ring or heteroaryl ring is fused to one or more other heteroaryl rings (e.g., for purposes of exemplification, which should not be construed as limiting the scope of this invention: benzo(b)thienyl, benzimidazolyl, benzoxazolyl, benzothiazolyl, benzothiadiazolyl, benzoxadiazolyl, indole, tetrahydroindole, azaindole, indazole, quinoline, imidazopyridine, quinazoline purine, pyrrolo[2,3-d]pyrimidine, pyrazolo[3,4-d]pyrimidine) and their N-oxides. Substituted heteroaryl groups are preferably substituted with one or more substituents each independently selected from the group consisting of a halogen, hydroxy, alkyl, alkoxy, alkyl-O—C(O)—, alkoxyalkyl, a heterocycloalkyl group, optionally substituted phenyl, nitro, amino, mono-substituted amino or di-substituted amino.

A heterocyclic (heterocyclyl) group, as used herein, refers to both heteroaryl groups and heterocycloalkyl groups.

A heterobicyclic group, as used herein, refers to a bicyclic group having one or more heteroatoms, which is saturated, partially unsaturated or unsaturated.

An arylalkyl group, as used herein, is an aromatic substituent that is linked to a compound by an aliphatic group having from one to about six carbon atoms. A preferred arylalkyl group is a benzyl group An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur. As used herein, aliphatic groups or notations such as "($C_0$–$C_6$)" include straight chained, branched or cyclic hydrocarbons which are completely saturated or which contain one or more units of unsaturation. When the group is a $C_0$ it means that the moiety is not present or in other words is a bond.

As used herein, aromatic groups (or aryl groups) include aromatic carbocyclic ring systems (e.g. phenyl) and fused polycyclic aromatic ring systems (e.g. naphthyl and 1,2,3,4-tetrahydronaphthyl).

As used herein, the term "natural amino acid" refers to the twenty-three natural amino acids known in the art, which are as follows (denoted by their three letter acronym): Ala, Arg, Asn, Asp, Cys, Cys—Cys, Glu, Gln, Gly, His, Hyl, Hyp, Ile, Leu, Lys, Met, Phe, Pro, Ser, Thr, Trp, Tyr, and Val. The term non-natural amino acid refers to compounds of the formula $NH_2$—$(C(X)_2)_n$—COOH, which are alpha- (when n is 1) or beta- (when n is 2) amino acids where X for each occurrence is independently any side chain moiety recognized by those skilled in the art; examples of non-natural amino acids include, but are not limited to: hydroxyproline, homoproline, 4-amino-phenylalanine, β-(2-naphthyl)alanine, norleucine, cyclohexylalanine, β-(3-pyridinyl)alanine, β-(4-pyridinyl)alanine, α-aminoisobutyric acid, urocanic acid, N,N-tetramethylamidino-histidine, N-methyl-alanine, N-methylglycine, N-methyl-glutamic acid, tert-butylglycine, α-aminobutyric acid, tert-butylalanine, ornithine, α-aminoisobutyric acid, β-alanine, γ-aminobutyric acid, 5-aminovaleric acid, 12-aminododecanoic acid, 2-aminoindane-2-carboxylic acid, etc. and the derivatives thereof, especially where the amine nitrogen has been mono- or di-alkylated.

As used herein, many moieties or substituents are termed as being either "substituted or unsubstituted" or "optionally substituted". When a moiety is modified by one of these terms, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkyl groups (which itself can also be substituted, such as $CF_3$), alkoxy group (which itself can be substituted, such as $OCF_3$), a halogen or halo group (F, Cl, Br, I), hydroxy, nitro, oxo, CN, COH, COOH, amino, N-alkylamino or N,N-dialkylamino (in which the alkyl groups can also be substituted), esters (—C(O)—OR, where R is groups such as alkyl, aryl, etc., which can be substituted), aryl (most preferred is phenyl, which can be substituted) and arylalkyl (which can be substituted).

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer *Helicobacter* related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention are useful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7–10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Flt-4/VEGFR-3, Tie-1, Tie-2, FGFR, PDGFR, IGF-R, c-Met, Src-subfamily kinases such as Lck, hck, fgr, Src, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising adiminstering to the patient a therapeutically or prophylactically effective amount of one or more compounds of Formulas 1–109.

A "protein kinase-mediated condition" or a "condition mediated by protein kinase activity"is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of Formulas 1–109 or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficincy virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, postlaser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

The Src, Tec, Jak, Map, Csk, NFκB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formulas 1–109 may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formulas 1–109, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF-promoted smooth muscle and endothelial cell proliferation. The ligand stimulation of FGFR, PDGFR, IGF 1-R and c-Met in vivo is proangiogenic, and potentiates angiogenesis dependent disorders. Inhibition of FGFr, PDGFr, c-Met, or IGF 1-R kinase activities individually or in combination may be an efficacious strategy for inhibiting these phenomena. Thus compounds of formulas 1–109 which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDR/VEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (J. Clin. Investig. 103: 1231–1236 (1999)). In some progenitors, Tie-2 may play a role in their recruitment, adhesion, regulation and differentiation (Blood, 4317–4326 (1997)). Certain agents according to formulas 1–109 capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055–1066 (1999)). In an analogous manner a Tie-2 kinase inhibitor can be proangiogenic or antiangiogenic in the presence or absence of a VEGF-related stimulus, respectively.

The compounds of formulas 1–109 or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection. (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates; including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formulas 1–109 as defined initially above for use as medicaments, particularly as inhibitors of protein kinase activity for example tyrosine kinase activity, serine kinase activity and threonine kinase activity. In yet another aspect the present invention provides the use of compounds of formulas 1–109 as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Phamaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric coated tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors and P13 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formulas 1–109 as a medicament.

A further aspect of the present invention provides the use of a compound of formulas 1–109 or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formulas 1–109 to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536–539) by a test compound relative to control.

KDR Tyrosine Kinase Production Using Baculovirus System:

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$ KDR(aa789–1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from IL of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775–1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 μl) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids $M(H)_6 LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The LVPR$_9$S bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 g/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Ca.)) or purified from known natural or recombinant sources using conventional methods.

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu$_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM MgCl$_2$, 4 mM MnCl$_2$, 5 mM DTT, 0.02% BSA, 200 µM NaVO$_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 µl, e.g. for KDR make to 1 ng/µl for a total of 50 ng per well in the reactions. Store on ice.

Make 4× ATP solution to 20 µM from 100 mM stock in water. Store on ice

Add 50 µl of the enzyme solution per well (typically 5–50 ng enzyme/well depending on the specific activity of the kinase)

Add 25 µl 4× inhibitor

Add 25 µl 4× ATP for inhibitor assay

Incubate for 10 minutes at room temperature

Stop reaction by adding 50 µl 0.05N HCl per well

Wash plate

**Final Concentrations for Reaction: 5 µM ATP, 5% DMSO

3. Antibody Binding

Dilute 1 mg/ml aliquot of PY20—HRP (Pierce) antibody (a phosphotyrosine antibody) to 50 ng/ml in 0.1% BSA in PBS by a 2 step dilution (100×, then 200×)

Add 100 µl Ab per well. Incubate 1 hr at room temp. Incubate 1 hr at 4 C.

Wash 4× plate

4. Color reaction

Prepare TMB substrate and add 100 µl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM MnCl$_2$, 20 mM MgCl$_2$, 5 mM DTT, 0.2% BSA, 200 mM NaVO$_4$ under the analogous assay conditions.

Compounds of formulas 1–109 may have therapeutic utility in the treatment of diseases involving both identified, including those not mentioned herein, and as yet unidentified protein tyrosine kinases which are inhibited by compounds of formulas 1–109.

Cdc2 Source

The human recombinant enzyme and assay buffer may be obtained commercially (New England Biolabs, Beverly, Mass. USA) or purified from known natural or recombinant sources using conventional methods.

Cdc2 Assay

A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 µM ATP (31 µCi/ml) and 30 µg/ml histone type IIIss final concentrations. A reaction volume of 80 µL, containing units of enzyme, is run for 20 minutes at 25 degrees C. in the presence or absence of inhibitor. The reaction is terminated by the addition of 120 µL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source

The catalytic subunit of PKC may be obtained commercially (Calbiochem).

PKC Kinase Assay

A radioactive kinase assay is employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions are performed in a kinase buffer consisting of 50 mM Tris-HCl pH7.5, 10 mM MgCl$_2$, 2 mM DTT, 1 mM EGTA, 100 µM ATP, 8 µM peptide, 5% DMSO and $^{33}$P ATP (8 Ci/mM). Compound and enzyme are mixed in the reaction vessel and the reaction is initiated by addition of the ATP and substrate mixture. Following termination of the reaction by the addition of 10 µL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction is carried out in a buffer consisting of 50 mM Tris pH 7.5, 1 mM EGTA, 2 mM DTT, 0.01% Brij, 5% DMSO and 10 mM MgCl$_2$ (commercial buffer) supplemented with fresh 100 µM ATP (31 µCi/ml) and 30 µM myelin basic protein under conditions recommended by the supplier. Reaction volumes and method of assaying incorporated radioactivity are as described for the PKC assay (vide supra).

In Vitro Models for T-Cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 µl volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2-mercaptoethanol and 0.5% DMSO, The cultures are pulsed with 0.5 µCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model: J. Immunol 146(4): 1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701–17D6, 1994) or heart (Am. J. Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3–8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at $0.5–1.0 \times 10^5$ cells/well in each well of 6-well cluster plates (Costar; Cambridge, Mass.).

3. 3–4 days after seeding, plates are typically 90–100% confluent. Medium is removed from all the wells, cells are rinsed with 5–10 ml of PBS and incubated 18–24 h with 5 ml of EBM base media with no supplements added (i.e., serum starvation).

4. Serial dilutions of inhibitors are added in 1 ml of EBM media (25 µM, 5 µM, or 1 µM final concentration to cells and incubated for one hour at 37 C. Human recombinant $VEGF_{165}$ (R & D Systems) is then added to all the wells in 2 ml of EBM medium at a final concentration of 50 ng/ml and incubated at 37 C. for 10 minutes. Control cells untreated or treated with VEGF only are used to assess background phosphorylation and phosphorylation induction by VEGF.

All wells are then rinsed with 5–10 ml of cold PBS containing 1 mM Sodium Orthovanadate (Sigma) and cells are lysed and scraped in 200 µl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 µg/ml, pepstatin 1 µg/ml, leupeptin 1 µg/ml, Na vanadate 1 mM, Na fluoride 1 mM) and 1 µg/ml of Dnase (all chemicals from Sigma Chemical Company, St Louis, Mo.). The lysate is spun at 14,000 rpm for 30 min, to eliminate nuclei.

Equal amounts of proteins are then precipitated by addition of cold (−20 C.) Ethanol (2 volumes) for a minimum of 1 hour or a maximum of overnight. Pellets are reconstituted in Laemli sample buffer containing 5%-mercaptoethanol (BioRad; Hercules, Calif.) and boiled for 5 min. The proteins are resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated $F(ab)_2$ of goat anti-rabbit or goat-anti-mouse IgG the bands are visualized using the emission chemiluminescience (ECL) system (Amersham Life Sciences, Arlington Height, Ill.).

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions.

Vehicle components (DMSO, Cremaphor EL) can be purchased from Sigma (St. Louis, Mo.).

Mice (Balb/c, 8–12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5–10. Test compounds are administered by i.p., i.v. or p.o. routes depending on solubility and vehicle at doses ranging from 1–100 mg/kg. Vehicle control group receive vehicle only and two groups are left untreated.

Thirty minutes later, experimental, vehicle and 1 of the untreated groups are given an i.p. injection of 17-estradiol (500 µg/kg). After 2–3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

EXAMPLE 1

7-Cyclopentyl-5-(4-phenoxyphenyl)-5H-pyrrolo[3,2-d]pyrimidin-4-amine a) 2-cyclopentylacetonitrile A mixture of sodium hydride (2.17 g, 60% in oil, 54.2 mmol) in diethyl ether (100 mL) was cooled to 0° C. then treated with diethyl(cyanomethyl) phosphonate (9.6 g, 54.2 mmol) while maintaining the temperature of the mixture at less than 0° C. Cyclopentanone (4.13 g, 49.3 mmol) in diethyl ether (25 mL) was added to the mixture at less than 5° C. then the reaction was warmed to ambient temperature and stirred for an additional 16 hours. Water (240 mL) was added to the mixture and the layers were then separated. The aqueous layer was extracted with diethyl ether (50 mL). The combined organic solutions were extracted with water (50 mL) then brine (50 mL) and finally dried over magnesium sulfate, filtered and the filtrate concentrated under reduced pressure. The resulting residue was dissolved in ethanol (40 mL) then 10% palladium on carbon (250 mg) was added and the mixture hydrogenated at atmospheric pressure and ambient temperature for 16 hours. The catalyst was removed by filtration through a pad of celite and the filtrate concentrated to an oil under reduced pressure. The title compound was purified by fractional distillation to give 4.08 g (75.6%) as a light yellow oil (boiling point 63° C. at 20 torr).: $^1$H NMR (Chloroform-d, 400 MHz) δ 2.35 (d, 2H), 2.18 (m, 1H), 1.87 (m, 2H), 1.59–1.69 (m, 4H), 1.29 (m, 2H).

b) 1-cyclopentyl-2-oxoethylcyanide

A mixture of 2-cyclopentylacetonitrile (0.50 g, 4.59 mmol) in tetrahydrofuran (10 mL) was cooled to −60° C. then treated with 1.7 M tert-buytllithium in pentane (3.25 mL, 5.50 mmol) while maintaining the reaction temperature at less than −55° C. The solution was stirred for 10 minutes then ethyl formate (0.41 g, 5.50 mmol) was added dropwise. The mixture was warmed to ambient temperature and stirred an additional 16 hours. The mixture was concentrated under reduced pressure and the resulting residue applied to a silica gel column and eluted with dichloromethane/ethyl acetate (95:5). The fractions containing material with an $R_f$ of 0.1–0.3 [TLC, dichloromethane/ethyl acetate (95:5), potassium permanganate stain] were combined and concentrated to give an oil which was used without further purification: $^1$H NMR (Chloroform-d, 400 MHz) δ 9.57 (s, 1H), 3.54 (d, 1H), 2.45 (m, 1H), 1.4–1.9 (m, 8H).

c) (4-phenoxyanilino)methyl cyanide

A mixture of 4-phenoxyaniline (7.0 g, 37.8 mmol), bromoacetonitrile (4.5 g, 37.8 mmol) and triethylamine (4.2 g, 41.6 mmol) in tetrahydrofuran (50 mL) was heated at 85° C. for 5.25 hours then cooled and another portion of bromoacetonitrile (6.5 g, 5.46 mmol) was added. The mixture was heated at 85° C. for 18 hours then cooled and concentrated under reduced pressure. The residue was partitioned between dichloromethane (50 mL) and water (50 mL). The aqueous layer was extracted with dichloromethane (30 mL) then the combined organic solutions were extracted with 5 N aqueous sodium hydroxide (30 mL), dried over magnesium sulfate, filtered and the filtrate concentrated under reduced pressure. The residue was then purified by flash chromatography on silica gel using dichloromethane/ethyl acetate (98:2) as an eluent to provide 3.8 g (45%) of the title compound as a dark brown solid: $^1$H NMR (DMSO-$d_6$, 400 MHz) δ 7.32 (t, 2H), 7.03 (t, 1H), 6.87–6.94 (m, 4H), 6.76 (d, 2H), 6.26 (bs, 2H), 4.25 (s, 2H);RP-HPLC (Hypersil HS-C18, 5 μm, 100 A, 4.6×250 mm; 25%–100% acetonitrile-0.05 M ammonium acetate over 25 min, 1 mL/min) $t_r$ 18.4 min.; MS: MH$^+$ 225.1.

d) 3-amino-4-cyclopentyl-1-(4-phenoxyphenyl)-1H-2-pyrrolecarbonitrile

A mixture of (4-phenoxyanilino)methyl cyanide (0.68 g, 3.30 mmol) and 1-cyclopenytl-2-oxoethylcyanide (0.54 g, 3.94 mmol) in 1,2-dimethoxyethane (10 mL) was treated with 2 drops of acetic acid then heated at 85° C. for 45 minutes. The mixture was cooled to ambient temperature then 1,5-diazabicyclo[4.3.0]non-5-ene (DBN) (1.13 g, 9.09 mmol) was added. The mixture was then heated at 65° C. for 16 hours and 85° C. for 6 -hours. Fresh DBN (0.25 mL) was added and the mixture was heated at 85° C. for an additional 18 hours. The solvent was removed under reduced pressure then the residue was applied to a silica gel column and eluted with heptane/ethyl acetate (7:3) to provide 185 mg (17.8%) of the title compound as a glass: $^1$H NMR (DMSO-$d_6$, 400 MHz) δ 7.42 (m, 4H), 7.17 (t, 1H), 7.04–7.11 (m, 4H), 6.99 (s, 1H), 5.10 (bs, 2H), 2.82 (m, 1H), 1.97 (m, 2H), 1.69 (m, 2H), 1.58 (m, 2H); RP-HPLC (Hypersil HS-C18, 5 μm, 100 A, 4.6×250 mm; 25%–100% acetonitrile-0.05 M ammonium acetate over 25 min, 1 mL/min) $t_r$ 26.2 min.; MS: MH$^+$ 343.9.

e) 7-cyclopentyl-5-(4-phenoxyphenyl)-5H-pyrrolo [3,2-d]pyrimidin-4-amine

A mixture of the 3-amino-4-cyclopentyl-1-(4-phenoxyphenyl)-1H-2-pyrrolecarbonitrile (185 mg, 0.539 mmol) in absolute ethanol (10 mL) was treated with formamidine acetate (450 mg, 4.33 mmol) then heated at 85° C. for 2 hours. The solvent was evaporated under reduced pressure then the residue was purified by preparative reverse phase HPLC to provide 145 mg (73%) of the title compound as a white solid after lyophilization: $^1$H NMR (DMSO-$d_6$, 400

MHz) δ 8.19 (s, 1H), 7.44 (m, 5H), 7.19 (t, 1H), 7.13 (m, 4H), 5.79 (bs, 2H), 3.23 (m, 1H), 2.05 (m, 2H), 1.77 (m, 4H), 1.64 (m, 2H); RP-HPLC (Hypersil HS-C18, 5 μm, 100 A, 4.6×250 mm; 5%–100% acetonitrile-0.05 M ammonium acetate over 25 min, 1 mL/min) $t_r$ 23.3 min.; MS: MH$^+$ 371.5.

EXAMPLE 2

1-cyclopentyl-3-(4-phenoxyphenyl)-1H-pyrrolo-[2,3-d]pyridazin-4-amine a) Ethyl 3-cyano-1-cyclopentyl-1H-2-pyrrolocarboxylate The title compound was prepared from cyclopentyl amine and diethyl (2E,4E,6E)-3,6-dicyano-2,7-dihydroxy-2,4,6-octatriendioate in a 13% yield by the method described by Huisgen[1]: $^1$H NMR (DMSO-$d_6$, 400 MHz) δ 7.47 (d, 1H), 6.72 (d, 1H), 5.37 (m, 1H), 4.31 (q, 2H), 2.11 (m, 2H), 1.77 (m, 4H), 1.66 (m, 2H), 1.32 (t, 3H); RP-HPLC (Hypersil HS-C18, 5 μm, 100 A, 4.6×250 mm; 5%–100% acetonitrile-0.05 M ammonium acetate over 25 min, 1 mL/min) $t_r$ 22.2 min.

b) 3-cyano-1-cyclopentyl-1H-2-pyrrolocarboxylic acid

A mixture of ethyl 3-cyano-1-cyclopentyl-1H-2-pyrrolocarboxylate (1.15 g, 5.16 mmol) in ethanol (25 mL) and water (5 mL) was treated with potassium hydroxide (0.58 g, 10.32 mmol). The mixture was heated at 75° C. for 30 minutes then cooled and the solvents evaporated under reduced pressure. Water (20 mL) was added and the solution was cooled to 0° C. then acidified with concentrated hydrochloric acid (1.3 g, 36% by weight, 11.35 mmol). The slurry that formed was stirred for 10 minutes then the solid was collected by filtration to give the title compound (0.75 g, 75%) as a light orange solid.: $^1$H NMR (DMSO-$d_6$, 400 MHz) δ 13.49 (bs, 1H), 7.41 (d, 1H), 6.67 (d, 1H), 5.47 (m, 1H), 22.09 (m, 2H), 1.77 (m, 4H),1 1.64 (m, 2H); RP-HPLC (Hypersil HS-C18, 5 μm, 100 A, 4.6×250 mm; 5%–100% acetonitrile-0.05 M ammonium acetate over 25 min, 1 mL/min) $t_r$ 12.52 min.

c) 1-cyclopentyl-2-formyl-1H-3-pyrrolecarbonitrile

A mixture of 3-cyano-1-cyclopentyl-1H-2-pyrrolocarboxylic acid (0.75 g, 3.68 mmol) in dichloromethane (5 mL) was cooled to 0° C. then treated with oxalyl chloride (0.52 g, 4.04 mmol). N,N-Dimethylformamide (1 drop) was added then the mixture was warmed to ambient temperature and stirred for 1.5 hours. The solvents were removed under reduced pressure then the residue was dissolved in diglyme (10 mL). The solution which resulted was cooled to −60° C. then lithium tri-tert-butoxyaluminohydride (8 mL, 0.5 M solution in diglyme, 4.0 mmol) was added dropwise over the course of approximately 1.5 hours while maintaining the temperature of the solution below −60° C. The mixture was allowed to warm to −10° C. then it was cooled to −60° C. and an additional portion of 0.5 M lithium tri-tert-butoxyaluminohydride in diglyme was added (1.5 mL, 0.75 mmol). The mixture was warmed to ambient temperature then treated with concentrated hydrochloric acid (1 mL) and purified by preparative reverse phase HPLC to provide the title compound (200 mg, 30%): $^1$H NMR (DMSO-$d_6$, 400 MHz) δ 9.82 (s, 1H), 7.60 (d, 1H), 6.84 (d, 1H), 5.32 (m, 2H), 2.10 (m, 2H), 1.81 (m, 4H), 1.66 (m, 2H); 5%–100% acetonitrile-0.05 M ammonium acetate over 25 min, 1 mL/min) $t_r$ 19.46 min.; GC/MS: MH$^+$ 189.2.

d) 1-cyclopentyl-1H-pyrrolo[2,3-d]pyridazin-4-amine

A mixture of 1-cyclopentyl-2-formyl-1H-3-pyrrolecarbonitrile (0.525 g, 2.79 mmol) and hydrazine dihydrochloride (0.35 g, 3.35 mmol) in ethanol (30 mL) was heated at reflux for 2.5 hours then cooled to ambient temperature and purified by preparative reverse phase HPLC to give the title compound as a hydroscopic glass contaminated with ammonium acetate (594 mg) (60% by weight as determined by $^1$H NMR, yield=337 mg; $^1$H NMR (DMSO-$d_6$, 400 MHz) δ 8.83 (s, 1H), 7.55 (d, 1H), 6.71 (d, 1H), 6.10 (bs, 2H), 4.94 (m, 1H), 2.15 (m, 2H), 1.89 (m, 4H), 1.70 (m, 2H); 5%–100% acetonitrile-0.05 M ammonium acetate over 25 min, 1 mL/min) $t_r$ 19.46 min.; LC/MS: MH$^+$ 203.0.

e) 3-bromo-1-cyclopentyl-1H-pyrrolo[2,3-d]pyridazin-4-amine

A mixture of 1-cyclopentyl-1H-pyrrolo[2,3-d]pyridazin-4-amine (0.595 mg, approx. 60% pure, 1.76 mmol) in dichloromethane (100 mL) was treated with a solution of dichloromethane (5 mL) containing bromine (0.5 g, 2.95 mmol) over the course of 1.25 hours. The mixture was stirred an additional one hour then another portion of dichloromethane (3 mL) containing bromine (0.3 g) was added. The mixture was stirred for 2.5 hours then treated with 5 mL 5N aqueous sodium hydroxide and 25 mL water. The layers were separated and the organic layer was concentrated under reduced pressure to give a residue which was purified by reverse phase preparative HPLC to give 3-bromo-1-cyclopentyl-1H-pyrrolo[2,3-d]pyridazin-4-amine (168 mg, 35%); $^1$H NMR (DMSO-$d_6$, 400 MHz) δ 8.94 (s, 1H), 7.79 (s, 1H), 6.11 (bs, 2H), 4.94 (m, 1H), 2.12 (m, 2H), 1.83 (m, 4H), 1.67 (m, 2H); 5%–100% acetonitrile-0.05 M ammonium acetate over 25 min, 1 mL/min) $t_r$ 11.25 min.; LC/MS: MH$^+$ 282.8.

f) 1-cyclopentyl-3-(4-phenoxyphenyl)-1H-pyrrolo-[2,3-d]pyridazin-4-amine

A mixture of 3-bromo-1-cyclopentyl-1H-pyrrolo [2,3-d]pyridazin-4-amine (0.057 g, 0.178 mmol), 4-phenoxyphenyl boronic acid (0.057 g, 0.266 mmol), sodium carbonate (0.062 g, 0.588 mmol) and tetrakis(triphenylphosphine)palladium(0) (12 mg, 0.011 mmol) in ethylene glycol dimethyl ether (3 mL) and water (1.5 mL) was heated at 85° C. under an atmosphere of nitrogen for 2.5 hours. The mixture was cooled to ambient temperature and the solvent evaporated under reduced pressure. The residue was purified by preparative reverse phase HPLC to give the title compound contaminated with 4-phenoxyphenyl boronic acid. The residue was partitioned between dichloromethane and 5 N aqueous sodium hydroxide. The organic layer was dried over magnesium sulfate, filtered and the filtrate evaporated to give the title compound (14 mg, 21%); $^1$H NMR (DMSO-$d_6$, 400 MHz) δ 8.98 (s, 1H), 7.68 (s, 1H),, 7.50 (d, 2H), 7.40 (t, 2H), 7.17 (t, 1H), 7.09 (m, 4H), 5.76 (bs, 2H), 5.01 (m, 1H), 2.19 (m, 2H), 1.91 (m, 2H), 1.71 (m, 2H); 5%–100% acetonitrile-0.05 M ammonium acetate over 25 min, 1 mL/min) $t_r$ 20.60 min.; LC/MS: MH$^+$ 371.2.

(1) Huisgen, R.; Laschtuvka, E. Eine Neue Syntheses von Derivaten des Pyrroles. Chem. Ber. 1960, 93, 65.

Other preferred compounds of the instant invention are those compounds where the compound of Formula (I) is

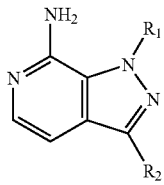

wherein
R₁=trans-2-phenyl-cyclopropanecarboxamide
  phenyl-4-(trifluoromethyl)benzamide
  phenyl-1-methyl-2-indolecarboxamide
  phenyl-2,2-dimethyl-3-phenylpropanamide
  phenoxyphenyl
R₂=cyclopentyl
  cis-cyclohexyl piperazine
  trans-cyclohexyl piperazine
  piperazinyl-piperizinyl More specifically, the compounds are:
N1-[4-(7-amino-3-cyclopentyl-1H-pyrazolo[3,4-c]pyridin-1-yl)phenyl]-trans-2-phenylcyclopropane-1-carboxamide;
Cis-N1-(4-{7-amino-3-[4-(4-methylpiperazino)cyclohexyl]-1H-pyrazolo[3,4-c]pyridin-1-yl}phenyl)-trans-2-phenylcyclopropane-1-carboxamide;
Trans-N1-(4-{7-amino-3-[4-(4-methylpiperazino)cyclohexyl]-1H-pyrazolo[3,4-c]pyridin-1-yl}phenyl)-trans-2-phenylcyclopropane-1-carboxamide;
N1-(4-{7-amino-3-[(1-methylpiperidin-4-yl)piperidin-4-yl]-1H-pyrazolo[3,4-c]pyridin-1-yl}phenyl)-2-phenyl-1-cyclopropanecarboxamide;
N1-[4-(7-amino-3-cyclopentyl-1H-pyrazolo[3,4-c]pyridin-1-yl)phenyl]-4-(trifluoromethyl)benzamide;
Cis-N1-(4-{7-amino-3-[4-(4-methylpiperazino)cyclohexyl]-1H-pyrazolo[3,4-c]pyridin-1-yl}phenyl)-4-(trifluoromethyl)benzamide;
Trans-N1-(4-{7-amino-3-[4-(4-methylpiperazino)cyclohexyl]-1H-pyrazolo[3,4-c]pyridin-1-yl}phenyl)-4-(trifluoromethyl)benzamide;
N1-(4-{7-amino-3-[(1-methylpiperidin-4-yl)piperidin-4-yl]-1H-pyrazolo[3,4-c]pyridin-1-yl}phenyl)-4-(trifluoromethyl)benzamide;
N2-[4-(7-amino-3-cyclopentyl-1H-pyrazolo[3,4-c]pyridin-1-yl)phenyl]-1-methyl-1H-2-indolecarboxamide;
Cis-N2-(4-{7-amino-3-[4-(4-methylpiperazino)cyclohexyl]-1H-pyrazolo[3,4-c]pyridin-1-yl}phenyl)-1-methyl-1H-2-indolecarboxamide;
Trans-N2-(4-{7-amino-3-[4-(4-methylpiperazino)cyclohexyl]-1H-pyrazolo[3,4-c]pyridin-1-yl}phenyl)-1-methyl-1H-2-indolecarboxamide;
N2-(4-{7-amino-3-[(1-methylpiperidin-4-yl)piperidin-4-yl]-1H-pyrazolo[3,4-c]pyridin-1-yl}phenyl)-1-methyl-1H-2-indolecarboxamide;
N1-[4-(7-amino-3-cyclopentyl-1H-pyrazolo[3,4-c]pyridin-1-yl)phenyl]-2,2-dimethyl-3-phenylpropanamide;
Cis-N1-(4-{7-amino-3-[4-(4-methylpiperazino)cyclohexyl]-1H-pyrazolo[3,4-c]pyridin-1-yl}phenyl)-2,2-dimethyl-3-phenylpropanamide;
Trans-N1-(4-{7-amino-3-[4-(4-methylpiperazino)cyclohexyl]-1H-pyrazolo[3,4-c]pyridin-1-yl}phenyl)-2,2-dimethyl-3-phenylpropanamide;
N1-(4-{7-amino-3-[(1-methylpiperidin-4-yl)piperidin-4-yl]-1H-pyrazolo[3,4-c]pyridin-1-yl}phenyl)-2,2-dimethyl-3-phenylpropanamide;
3-cyclopentyl-1-(4-phenoxyphenyl)-1H-pyrazolo[3,4-c]pyridin-7-amine;
Cis-3-[4-(4-methylpiperazino)cyclohexyl]-1-(4-phenoxyphenyl)-1H-pyrazolo[3,4-c]pyridin-7-amine;
Trans-3-[4-(4-methylpiperazino)cyclohexyl]-1-(4-phenoxyphenyl)-1H-pyrazolo[3,4-c]pyridin-7-amine; and
3-[(1-methylpiperidin-4-yl)piperidin-4-yl]-1-(4-phenoxyphenyl)-1H-pyrazolo[3,4-c]pyridin-7-amine.

Other preferred compounds include:
7-cyclopentyl-5-(4-phenoxyphenyl)-5H-pyrrolo[3,2-d]pyrimidin-4-amine;
1-cyclopentyl-3-(4-phenoxyphenyl)-1H-pyrrolo[2,3-d]pyridazin-4-amine;
4-amino-9-cyclopentyl-6-(4-phenoxyphenyl)-6,7,8,9-tetrahydro-5H-pyrimido[4,5-b][1,4]diazepin-8-one; and
4-amino-9-cyclopentyl-6-(4-phenoxyphenyl)-8,9-dihydro-5H-pyrimido[4,5-b][1,4]diazepin-8-one.

The foregoing compounds can be synthesized substantially according to Examples 1 or 2 using the appropriate starting materials.

We claim:
1. A compound of Formula (I), the racemic-diastereomeric mixtures, optical isomers or pharmaceutically-acceptable salts thereof,

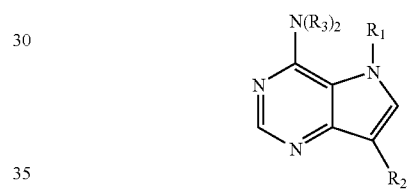

wherein:

R₁ is

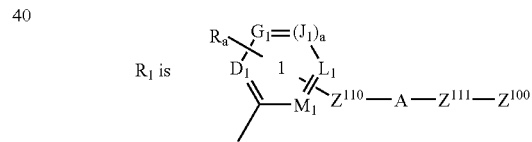

where $Z^{100}$ is

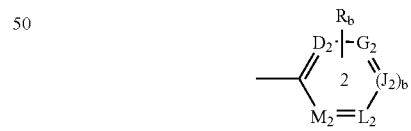

or a group optionally substituted with $R_b$ selected from the group consisting of cycloalkyl, naphthyl, tetrahydronaphthyl, benzothienyl, furanyl, thienyl, benzoxazolyl, benzothiazolyl,

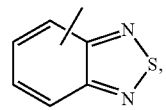

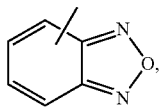

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted straight chained, branched or cyclic hydrocarbon which is completely saturated or which contains one or more units of unsaturation, which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted straight chained, branched or cyclic hydrocarbon which is completely saturated or which contains one or more units of unsaturation or an optionally substituted $—(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_b$ each represent one or more substituents for each occurrence independently selected from the group consisting of hydrogen, halogen, —CN, —$NO_2$, —C(O)OH, —C(O)H, —OH, —C(O)O-alkyl, substituted or unsubstituted carboxamido, tetrazolyl, trifluoromethylcarbonylamino, trifluoromethylsulfonamido, substituted or unsubstituted alkyl, substituted or unsubstituted alkoxy, substituted or unsubstituted aryl, substituted or unsubstituted alkenyl, substituted or unsubstituted aryloxy, substituted or unsubstituted heteroaryloxy, substituted or unsubstituted arylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -$Z^{105}$-C(O)N(R)$_2$, -$Z^{105}$-N(R)—C(O)-$Z^{200}$, -$Z^{105}$-N(R)—S(O)$_2$-$Z^{200}$, -$Z^{105}$-N(R)—C(O)—N(R)-$Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$—S-alkyl, or —W—$(CH_2)_t$—OH;

$Z^{105}$ for each occurrence is independently a covalent bond or straight chained, branched or cyclic hydrocarbon which is completely saturated or which contains one or more units of unsaturation;

$Z^{200}$ for each occurrence is independently a substituted or unsubstituted straight chained, branched or cyclic hydrocarbon which is completely saturated or which contains one or more units of unsaturation, substituted or unsubstituted phenyl or substituted or unsubstituted (straight chained, branched or cyclic hydrocarbon which is completely saturated or which contains one or more units of unsaturation)-phenyl;

$R_d$ and $R_e$ for each occurrence are independently H, alkyl, alkanoyl or $SO_2$-alkyl; or $R_d$, $R_e$ and the nitrogen atom to which they are attached together form pyridyl, pyrazolyl, isoxazolyl, thiadiazolyl, oxadiazolyl, furanyl, pyrrolyl, imidazolyl, pyrazolyl, triazolyl, pyrimidinyl, pyrazinyl, thiazolyl, isothiazolyl, oxazolyl or tetrazolyl ring; t for each occurrence is independently an integer from 2 to 6; W for each occurrence is independently a direct bond or O, S, S(O), $S(O)_2$, or $NR_f$, wherein $R_f$ for each occurrence is independently H or alkyl;

or $R_1$ is a substituted or unsubstituted carbocyclic, thienyl, pyridyl, pyrazolyl, isoxazolyl, thiadiazolyl, oxadiazolyl, indazolyl, furanyl, pyrrolyl, imidazolyl, pyrazolyl, triazolyl, pyrimidinyl, pyrazinyl, thiazolyl, isothiazolyl, oxazolyl, tetrazolyl, benzo[b]thienyl, benzimidazolyl, benzoxazolyl, benzothiazolyl, benzothiadiazolyl, benzodiazolyl, indolyl, tetrahydroindolyl, azaindolyl, indazolyl, quinolinyl, imidazopyridinyl, quinazoline purinyl, pyrrolo[2,3-d]pyrimidinyl, pyrazolo[3,4-d]pyrimidinyl or their N-oxides fused with ring 2;

$R_3$ is hydrogen, hydroxy, substituted or unsubstituted alkyl or substituted or unsubstituted alkoxy;

A is —O—; —S—; —S(O)$_p$—; —N(R)—; —N(C(O)OR)—; —N(C(O)R)—; —N(SO$_2$R)—; —$CH_2O$—; —$CH_2S$—; —$CH_2N(R)$—; —CH(NR)—; —$CH_2N(C(O)R)$—; —$CH_2N(C(O)OR)$—; —$CH_2N(SO_2R)$—; —CH(NHR)—; —CH(NHC(O)R)—; —CH(NHSO$_2$R)—; —CH(NHC(O)OR)—; —CH(OC(O)R)—; —CH(OC(O)NHR); —CH=CH—; —C(=NOR)—; —C(O)—; —CH(OR)—; —C(O)N(R)—; —N(R)C(O)—; —N(R)S(O)$_p$—; —OC(O)N(R)—;; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_g$)O—; —N(R)P(OR$_g$)—; —N(R)P(O)(OR$_g$)O—; —N(R)P(O)(OR$_g$)—; —N(C(O)R)P(OR$_g$)O—; —N(C(O)R)P(OR$_g$)—; —N(C(O)R)P(O)(OR$_g$)O—, or —N(C(O)R)P(OR$_g$)—;

where R for each occurrence is independently H, substituted or unsubstituted alkyl, substituted or unsubstituted arylalkyl or substituted or unsubstituted aryl;

$R_g$ for each occurrence is independently H, substituted or unsubstituted alkyl, substituted or unsubstituted arylalkyl, substituted or unsubstituted cycloalkyl or substituted or unsubstituted aryl;

p is 1 or 2;

or in a phosphorus containing group, the nitrogen atom, the phosphorus atom, R and $R_g$ together form a pyridyl, pyrazolyl, isoxazolyl, thiadiazolyl, oxadiazolyl, furanyl, pyrrolyl, imidazolyl, pyrazolyl, triazolyl, pyrimidinyl, pyrazinyl, thiazolyl, isothiazolyl, oxazolyl or tetrazolyl ring; or A is $NRSO_2$ and R, $R_a$ and the nitrogen atom together form a substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimidinyl, substituted or unsubstituted pyrazinyl, substituted or unsubstituted thiazolyl, substituted or unsubstituted isothiazolyl, substituted or unsubstituted oxazolyl or substituted or unsubstituted tetrazolyl ring fused to ring 1;

$R_2$ is $-Z^{101}-Z^{102}$;

$Z^{101}$ is a covalent bond, straight chained, branched or cyclic hydrocarbon which is completely saturated or which contains one or more units of unsaturation, straight chained, branched or cyclic hydrocarbon which is completely saturated or which contains one or more units of unsaturation-O—, straight chained, branched or cyclic hydrocarbon which is completely saturated or which contains one or more units of unsaturation-C(O)—, straight chained, branched or cyclic hydrocarbon which is completely saturated or which contains one or more units of unsaturation-C(O)O—, straight chained, branched or cyclic hydrocarbon which is completely saturated or which contains one or more units of unsaturation-C(O)—NH—, (straight chained, branched or cyclic hydrocarbon which is completely saturated or which contains one or more units of unsaturation)-C(O)—N (straight chained, branched or cyclic hydrocarbon which is completely saturated or which contains one or more units of unsaturation) or a substituted or unsubstituted phenyl group;

$Z^{102}$ is hydrogen, a substituted or unsubstituted alkyl group, a substituted or unsubstituted cycloalkyl group, a substituted or unsubstituted, thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimidinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline substituted or unsubstituted purinyl, substituted or unsubstituted pyrrolo[2,3-d]pyrimidinyl, substituted or unsubstituted pyrazolo[3,4-d]pyrimidinyl or their N-oxides, or a substituted or unsubstituted, saturated or unsaturated heterobicyclic group;

said substituted thienyl, substituted pyridyl, substituted pyrazolyl, substituted isoxazolyl, substituted thiadiazolyl, substituted oxadiazolyl, substituted indazolyl, substituted furanyl, substituted pyrrolyl, substituted imidazolyl, substituted pyrazolyl, substituted triazolyl, substituted pyrimidinyl, substituted pyrazinyl, substituted thiazolyl, substituted or isothiazolyl, substituted oxazolyl, substituted tetrazolyl, substituted benzo[b]thienyl, substituted benzimidazolyl, substituted benzoxazolyl, substituted benzothiazolyl, substituted benzothiadiazolyl, substituted benzodiazolyl, substituted indolyl, substituted tetrahydroindolyl, substituted azaindolyl, substituted indazolyl, substituted quinolinyl, substituted imidazopyridinyl, substituted quinazoline substituted purinyl, substituted pyrrolo[2,3-d]pyrimidinyl, substituted pyrazolo[3,4-d]pyrimidinyl or substituted heterobicyclic group having one or more substituents each independently selected from the group consisting of hydroxyl, cyano, substituted or unsubstituted alkoxy, substituted or unsubstituted sulfonamido, substituted or unsubstituted ureido, substituted or unsubstituted carboxamido; substituted or unsubstituted amino, oxo, a saturated, unsaturated or aromatic, substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimidinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, substituted or unsubstituted pyrazolo[3,4-d]pyrimidinyl or their N-oxides;

wherein said nitrogen atoms are independently optionally substituted by a substituted or unsubstituted alkyl, substituted or unsubstituted aryl or substituted or unsubstituted arylalkyl group; or $R_2$ is of the formula B-E, wherein B is a substituted or unsubstituted cycloalkyl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalklylcarbonyl, hydroxy, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted azacycloalkyl, substituted or unsubstituted azacycloalkylcarbonyl, substituted or unsubstituted azacycloalkylsulfonyl, substituted or unsubstituted azacycloalkylalkyl, substituted or unsubstituted heteroaryl, substituted or unsubstituted heteroarylcarbonyl, substituted or unsubstituted heteroarylsulfonyl, substituted or unsubstituted heteroarylalkyl, substituted or unsubstituted azacycloalkylcarbonylamino, substituted or unsubstituted heteroarylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

wherein the substituents for $R_a$, $R_b$, $R_c$, $Z^{200}$, $R_3$, $R_1$, $Z^{101}$, $Z^{102}$, B and E, are independently selected from the group consisting of alkyl, $CF_3$, alkoxy, $OCF_3$, halogen, hydroxyl, nitro, oxo, CN, COH, COOH, amino, N-alkylamino or N,N-dialkylamino, esters aryl, aryalkyl, alkyl-O—C(O), alkoxyalkyl, heterocycloalkyl, optionally substituted phenyl, nitro and optionally substituted amino.

2. The compound of claim 1 wherein $R_3$ is H; $R_1$ for each occurrence is independently selected from the group consisting of F, Cl, Br, I, $CH_3$, $NO_2$, $OCF_3$, $OCH_3$, CN, $CO_2CH_3$, $CF_3$, —$CH_2NR_dR_e$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

3. The compound of claim 1 wherein $R_3$ is H; $R_a$ for each occurrence is independently selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

4. The compound of claim 1 wherein $R_3$ is H; $R_2$ is of the formula

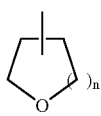

wherein n is 1, 2 or 3.

5. The compound of claim 1 wherein $R_3$ is H; $R_2$ is of the formula

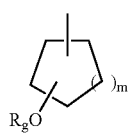

wherein m is 0, 1, 2 or 3 and $R_g$ is H or —$(CH_2)_pN(R_4)R_5$, wherein p is an integer from 2 to 6 and $R_4$ and $R_5$ are each, independently, H, azabicycloalkyl or Y-Z, wherein Y is selected from the group consisting of —C(O)—, —$(CH_2)_q$—, —S(O)$_2$—, —C(O)O—, —SO$_2$NH—, —CONH—, —$(CH_2)_qO$—, —$(CH_2)_qNH$—, and —$(CH_2)_qS(O)_r$—; wherein q is an integer from 0 to 6; and r is 0, 1 or 2; and Z is a substituted or unsubstituted moiety selected from the group consisting of alkyl, alkoxy, amino, aryl, heteroaryl and thienyl, pyridyl, pyrazolyl, isoxazolyl, thiadiazolyl, oxadiazolyl, indazolyl, furanyl, pyrrolyl, imidazolyl, pyrazolyl, triazolyl, pyrimdinyl, pyrazinyl, thiazolyl, isothiazolyl, oxazolyl, tetrazolyl, benzo[b]thienyl, benzimidazolyl, benzoxazolyl, benzothiazolyl, benzothiadiazolyl, benzodiazolyl, indolyl, tetrahydroindolyl, azaindolyl, indazolyl, quinolinyl, imidazopyridinyl, quinazoline purinyl, pyrrolo[2,3-d]pyrimidinyl, pyrazolo[3,4-d]pyrimidinyl or their N-oxides alkyl group or $R_4$, $R_5$ and the nitrogen atom to which they are attached together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, pyrazolo[3,4-d]pyrimidinyl or substituted or unsubstituted heterobicyclic group.

6. The compound of claim 1 wherein $R_3$ is H; $R_2$ is of the formula

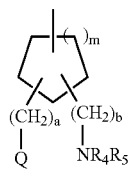

wherein m is 0, 1, 2 or 3 a and b are each, independently, an integer from 0 to 6;

Q is —$OR_6$ or —$NR_4R_5$;

each $R_4$ and $R_5$ is, independently, H, azabicycloalkyl or Y-Z, wherein Y is selected from the group consisting of —C(O)—, —$(CH_2)_q$—, —S(O)$_2$—, —C(O)O—, —SO$_2$NH—, —CONH—, $(CH_2)_qO$—, —$(CH_2)_q$NH—, and —$(CH_2)_qS(O)_r$—; wherein q is an integer from 0 to 6; and r is 0, 1 or 2; and Z is a substituted or unsubstituted alkyl, substituted or unsubstituted alkoxy, amino, aryl, heteroaryl or thienyl alkyl, pyridylalkyl, pyrazolylalkyl, isoxazolylalkyl, thiadiazolylalkyl, oxadiazolylalkyl, indazolylalkyl, furanylalkyl, pyrrolylalkyl, imidazolylalkyl, pyrazolylalkyl, triazolylalkyl, pyrimidinylalkyl, pyrazinylalkyl, thiazolylalkyl, isothiazolylalkyl, oxazolylalkyl, tetrazolylalkyl, benzo[b]thienylalkyl, benzimidazolylalkyl, benzoxazolylalkyl, benzothiazolylalkyl, benzothiadiazolylalkyl, benzodiazolylalkyl, indolylalkyl, tetrahydroindolylalkyl, azaindolylalkyl, indazolylalkyl, quinolinylalkyl, imidazopyridinylalkyl, quinazoline purinylalkyl, pyrrolo[2,3-d]pyrimidinyalkyl 1 or pyrazolo[3,4-d]pyrimidinylalkyl group or $R_4$, $R_5$ and the nitrogen atom to which they are attached together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, substituted or unsubstituted pyrazolo[3,4-d]pyrimidinyl or their N-oxides or substituted or unsubstituted heterobicyclic group; and $R_6$ is hydrogen or a substituted or unsubstituted alkyl group.

7. The compound of claim 1 wherein $R_3$ is H; $R_2$ is of the formula

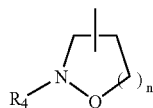

wherein n is 1, 2 or 3; and $R_4$ is H, azabicycloalkyl or Y-Z, wherein Y is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein q is an integer 0 to 6; and r is 0, 1 or 2; and Z is a substituted or unsubstituted alkyl, substituted or unsubstituted amino, aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group.

8. The compound of claim 1 wherein $R_3$ is H; $R_2$ is of the formula

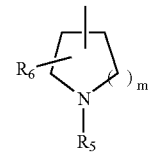

wherein m is 0, 1, 2 or 3;

$R_5$ is H, azabicycloalkyl or Y-Z, wherein Y is selected from the group consisting of a covalent bond, —C(O)—, —(CH$_2$)$_q$—, —S(O)$_2$—, —C(O)O—, —SO$_2$NH—, —CONH—, —(CH$_2$)$_q$O—, —(CH$_2$)$_q$NH, —(CH$_2$)$_q$C(O)—, —C(O)(CH$_2$)$_q$— and —(CH$_2$)$_q$S(O)$_r$—, where the alkyl portion of —(CH$_2$)$_q$—, —(CH$_2$)$_q$O—, —(CH$_2$)$_q$NH—, —(CH$_2$)$_q$C(O)—, —C(O)(CH$_2$)$_q$— and —(CH$_2$)$_q$S(O)$_r$ is optionally substituted by a halogen, hydroxy or an alkyl group;

wherein q is an integer from 0 to 6; and r is 0, 1 or 2; and Z is a substituted or unsubstituted alkyl, substituted or unsubstituted amino, substituted or unsubstituted alkoxy, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolyl alkyl, substituted or unsubstituted quinolinyl alkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group;

or Y and Z together are a natural or unnatural amino acid, which may be mono- or di-alkylated at the amine nitrogen; and $R_6$ represents one or more substituents each independently selected from the group consisting of hydrogen, hydroxy, oxo, substituted or unsubstituted alkyl, substituted or unsubstituted aryl, substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl, substituted or unsubstituted alkoxycarbonyl, substituted or unsubstituted alkoxyalkyl, substituted or unsubstituted aminocarbonyl, substituted or unsubstituted alkylcarbonyl, substituted or unsubstituted arylcarbonyl, substituted or unsubstituted heterocyclylcarbonyl, substituted or unsubstituted aminoalkyl and substituted or unsubstituted arylalkyl; provided that the carbon atoms adjacent to the nitrogen atom are not substituted by a hydroxy group.

9. The compound of claim 1 wherein $R_3$ is H; $R_2$ is of the formula

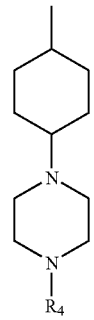

wherein $R_4$ is H, substituted or unsubstituted alkyl, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6, and r is 0, 1 or 2; and Z is hydrogen, substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl.

10. The compound of claim 1 wherein $R_3$ is H; $R_2$ is of the formula

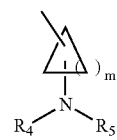

wherein m is an integer from 1 to 6; and $R_4$ and $R_5$ are each, independently, H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—;

wherein q is an integer from 0 to 6; and r is 0, 1 or 2; and Z is a substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or R$_4$, R$_5$ and the nitrogen atom to which they are attached together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl or substituted or unsubstituted heterobicyclic group.

11. The compound of claim 1 wherein R$_3$ is H; R$_2$ is of the formula

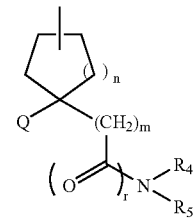

wherein n is an integer from 0 to 4;

r is 0 and m is an integer from 1 to 6; or r is 1 and m is an integer from 0 to 6;

Q is —OR$_6$ or —NR$_4$R$_5$;

each R$_4$ and R$_5$ is, independently, H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—;

q is an integer from 0 to 6; and r is 0, 1 or 2; and Z is a substituted or unsubstituted alkyl, substituted or unsubstituted alkoxy, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or R$_4$, R$_5$ and the nitrogen atom to which they are attached together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, or substituted or unsubstituted pyrazolo[3,4-d]pyrimidinyl group; and $R_6$ is hydrogen or a substituted or unsubstituted alkyl group.

12. The compound of claim 1 wherein $R_3$ is H; $R_2$ is of the formula

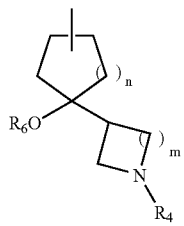

n is an integer from 0 to 4;

m is an integer from 0 to 6;

$R_4$ is H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl; and $R_6$ is hydrogen or a substituted or unsubstituted alkyl group.

13. The compound of claim 10 wherein $R_4$, $R_5$ and the nitrogen atom together form a heterocyclic group of the formula

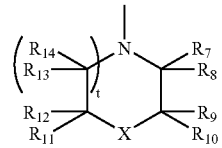

wherein $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), wherein $R_{15}$ and $R_{16}$ are each, independently, H, azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl; or $R_{15}$, $R_{16}$ and the nitrogen atom together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, substituted or unsubstituted pyrazolo[3,4-d]pyrimidinyl or a substituted or unsubstituted heterobicyclic group;

X is O, S, SO, $SO_2$, $CH_2$, $CHOR_{17}$ or $NR_{17}$, wherein $R_{17}$ is hydrogen, substituted or unsubstituted alkyl, substituted or unsubstituted aryl, substituted or unsubstituted arylalkyl, —C(NH)$NH_2$, —C(O)$R_{17}$, or —C(O)$OR_{18}$, wherein $R_{18}$ is hydrogen, substituted or unsubstituted alkyl, substituted or unsubstituted aryl or substituted or unsubstituted arylalkyl; and t is 0 or 1.

14. The compound of claim 10 wherein $R_4$, $R_5$ and the nitrogen atom together form a heterocycle of the formula

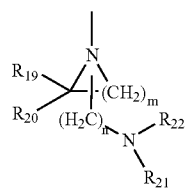

wherein
$R_{19}$ and $R_{20}$ are each, independently, hydrogen or lower alkyl; or $R_{19}$ and $R_{20}$ together are an oxygen atom;
$R_{21}$ and $R_{22}$ are each, independently, H, substituted or unsubstituted azabicycloalkyl or V-L, wherein V is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or $R_{21}$, $R_{22}$ and the nitrogen atom together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl group;

m is an integer from 1 to 6; and
n is an integer from 0 to 6.

15. The compound of claim 10 wherein $R_4$, $R_5$ and the nitrogen atom together form a heterocyclic group of the formula

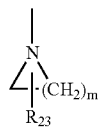

wherein m is an integer from 1 to 6; and $R_{23}$ is $CH_2OH$, NRR', C(O)NRR' or COOR, wherein R and R' are each, independently, hydrogen or substituted or unsubstituted alkyl, substituted or unsubstituted aryl or substituted or unsubstituted arylalkyl.

16. The compound of claim 10 wherein $R_4$, $R_5$ and the nitrogen atom together form a heterocyclic group of the formula

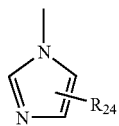

wherein $R_{24}$ is substituted or unsubstituted alkyl, substituted or unsubstituted aryl or substituted or unsubstituted arylalkyl, carboxyl, cyano, $C(O)OR_{25}$, $CH_2OR_{25}$, $CH_2NR_{26}R_{27}$ or $C(O)NHR_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl; and $R_{26}$ and $R_{27}$ are each, independently, H, substituted or unsubstituted azabicycloalkyl or V-L, wherein V is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinyl alkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl; or $R_{26}$, $R_{27}$ and the nitrogen atom together form a substituted or unsubstituted thienyl, pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl group.

17. The compound of claim 10 wherein at least one of $R_4$ and $R_5$ is of the formula Y-Z, wherein Z is of the formula

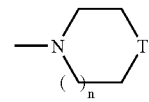

wherein

T is C(O), S, SO, $SO_2$, CHOR or NR, wherein R is hydrogen or a substituted or unsubstituted alkyl, substituted or unsubstituted aryl or substituted or unsubstituted arylalkyl group; and n is 0, 1 or 2.

18. The compound of claim 10 wherein at least one of $R_4$ and $R_5$ is of the formula Y-Z, wherein Z is of the formula —$N(R_{28})R_{29}$, wherein $R_{28}$ and $R_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted

115 or unsubstituted pyrimidinyl, substituted or unsubstituted pyrazinyl, substituted or unsubstituted thiazolyl, substituted or unsubstituted isothiazolyl, substituted or unsubstituted oxazolyl, or substituted or unsubstituted tetrazolyl group.

19. The compound of claim 11 wherein $R_4$, $R_5$ and the nitrogen atom together form a heterocycle of the formula

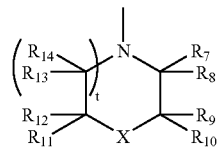

wherein $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, $CONHR_{15}$, $COOR_{15}$, $CH_2OR_{15}$ or $CH_2NR_{15}(R_{16})$, wherein $R_{15}$ and $R]_6$ are each, independently, H, substituted or unsubstituted azabicycloalkyl or V-L, wherein V is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl; or $R_{15}$, $R_{16}$ and the nitrogen atom together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl,

116 substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl or heterobicyclic group;

X is O, S, SO, $SO_2$, $CH_2$, $CHOR_{17}$ or $NR_{17}$, wherein $R_{17}$ is hydrogen, substituted or unsubstituted alkyl, substituted or unsubstituted aryl, substituted or unsubstituted arylalkyl, —C(NH)$NH_2$, —C(O)$R_{18}$, or —C(O)$OR_{18}$, wherein $R_{18}$ is hydrogen, substituted or unsubstituted alkyl, substituted or unsubstituted aryl or substituted or unsubstituted arylalkyl; and t is 0 or 1.

20. The compound of claim 11 wherein $R_4$, $R_5$ and the nitrogen atom together form a heterocycle of the formula

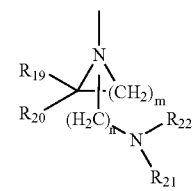

wherein $R_{19}$ and $R_{20}$ are each, independently, hydrogen or lower alkyl; or $R_{19}$ and $R_{20}$ together are an oxygen atom;

$R_{21}$ and $R_{22}$ are each, independently, H, substituted or unsubstituted azabicycloalkyl or V-L, wherein V is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or $R_{21}$, $R_{22}$ and the nitrogen atom together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl group;

m is an integer from 1 to 6; and n is an integer from 0 to 6.

21. The compound of claim 11 wherein $R_4$, $R_5$ and the nitrogen atom together form a heterocyclic group of the formula

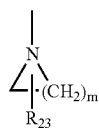

wherein m is an integer from 1 to 6; and $R_{23}$ is $CH_2OH$, NRR', C(O)NRR' or COOR, wherein R is hydrogen or a substituted or unsubstituted alkyl, substituted or unsubstituted aryl or substituted or unsubstituted arylalkyl group.

22. The compound of claim 11 wherein $R_4$, $R_5$ and the nitrogen atom together form a heterocyclic group of the formula

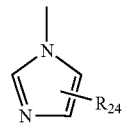

wherein $R_{24}$ is substituted or unsubstituted alkyl, substituted or unsubstituted aryl or substituted or unsubstituted arylalkyl, carboxyl, cyano, $C(O)OR_{25}$, $CH_2OR_{25}$, $CH_2NR_{26}R_{27}$ or $C(O)NHR_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl group; and $R_{26}$ and $R_{27}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or $R_{26}$, $R_{27}$ and the nitrogen atom together form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimdinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl or substituted or unsubstituted pyrazolo[3,4-d]pyrimidinyl group.

23. The compound of claim 11 wherein at least one of $R_4$ and $R_5$ is of the formula Y-Z, wherein Z is of the formula

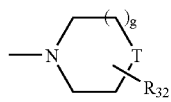

wherein g is 0 or 1;

T is C(O), O, S, SO, $SO_2$, $CH_2$, $CHOR_{17}$ or $NR_{17}$, wherein $R_{17}$ is hydrogen, substituted or unsubstituted alkyl, substituted or unsubstituted aryl, substituted or unsubstituted arylalkyl, —C(NH)$NH_2$, —C(O)$R_{18}$, or —C(O)O$R_{18}$, wherein $R_{18}$ is hydrogen, substituted or unsubstituted alkyl, substituted or unsubstituted aryl or substituted or unsubstituted arylalkyl; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl.

24. The compound of claim 11 wherein at least one of $R_4$ and $R_5$ is of the formula Y-Z, wherein Z is of the formula —N($R_{28}$)$R_{29}$, wherein $R_{28}$ and $R_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a substituted or unsubstituted thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimidinyl, substituted or unsubstituted pyrazinyl, substituted or unsubstituted thiazolyl, substituted or unsubstituted isothiazolyl, substituted or unsubstituted oxazolyl or substituted or unsubstituted tetrazolyl group.

25. The compound of claim 8 wherein $R_5$ is Y-Z, wherein Z is of the formula N($R_{30}$)$R_{31}$, wherein $R_{30}$ and $R_{31}$ are each, independently, hydrogen, alkyl, alkoxycarbonyl, alkoxyalkyl, hydroxyalkyl, aminocarbonyl, cyano, alkylcarbonyl or arylalkyl.

26. The compound of claim 8 wherein $R_5$ is Y-Z, wherein Z is of the formula

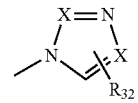

wherein each X is, independently, CH or N; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

27. The compound of claim 8 wherein $R_5$ is Y-Z, wherein Z is of the formula

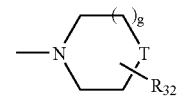

wherein g is 0 or 1;

T is O, S, SO, $SO_2$, $CH_2$, $CHOR_{17}$ or $NR_{17}$, wherein $R_{17}$ is hydrogen, substituted or unsubstituted alkyl, substituted or unsubstituted aryl, substituted or unsubstituted arylalkyl, C(O)$NH_2$, —C(NH)$NH_2$, —C(O)$R_{17}$, or —C(O)O$R_{18}$, wherein $R_{18}$ is hydrogen, substituted or unsubstituted alkyl, substituted or unsubstituted aryl or substituted or unsubstituted arylalkyl; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

28. The compound of claim 8 wherein $R_5$ is Y-Z, wherein Z is of the formula

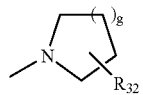

wherein g is 0, 1 or 2; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

29. The compound of claim 8 wherein $R_5$ is Y-Z, wherein Z is of the formula

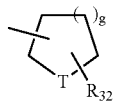

wherein

T is C(O), O, S, SO, $SO_2$, $CH_2$, $CHOR_{17}$ or $NR_{17}$, wherein $R_{17}$ is hydrogen, substituted or unsubstituted alkyl, aryl, arylalkyl, —C(NH)$NH_2$, —C(O)$R_{18}$, or —C(O)O$R_{18}$, wherein $R_{18}$ is hydrogen, substituted or unsubstituted alkyl, substituted or unsubstituted aryl or substituted or unsubstituted arylalkyl;

g is 0 or 1; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

30. The compound of claim 8 wherein $R_5$ is Y-Z, wherein Z is of the formula

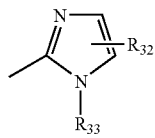

wherein $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, alkylcarbonyl, substituted or unsubstituted thioalkoxy or substituted or unsubstituted arylalkyl; and $R_{33}$ is hydrogen, substituted or unsubstituted alkyl, substituted or unsubstituted alkoxycarbonyl, substituted or unsubstituted alkoxyalkyl, substituted or unsubstituted aminocarbonyl, perhaloalkyl, substituted or unsubstituted alkenyl, substituted or unsubstituted alkylcarbonyl or substituted or unsubstituted arylalkyl.

31. The compound of claim 1 wherein $R_3$ is H; $R_2$ is of the formula

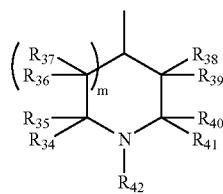

wherein m is 0 or 1;

$R_{34}$, $R_{35}$, $R_{36}$, $R_{37}$, $R_{38}$, $R_{39}$, $R_{40}$ and $R_{41}$ are each, independently, methyl or hydrogen; or at least one pair of substituents $R_{34}$ and $R_{35}$; $R_{36}$ and $R_{37}$; $R_{38}$ and $R_{39}$; or $R_{40}$ and $R_{41}$ together are an oxygen atom; and $R_{42}$ is H, substituted or unsubstituted azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl group; or $R_{42}$ is of the formula

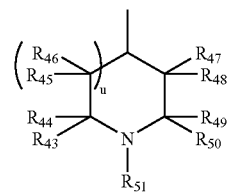

wherein u is 0 or 1;

$R_{43}$, $R_{44}$, $R_{45}$, $R_{46}$, $R_{47}$, $R_{48}$, $R_{49}$ and $R_{50}$ are each, independently, methyl or hydrogen;

or at least one pair of substituents $R_{43}$ and $R_{44}$; $R_{45}$ and $R_{46}$; $R_{47}$ and $R_{48}$; or $R_{49}$ and $R_{50}$ together are an oxygen atom; and $R_{51}$ is H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimidinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl.

32. The compound of claim 1 wherein $R_3$ is H; $R_2$ is of the formula

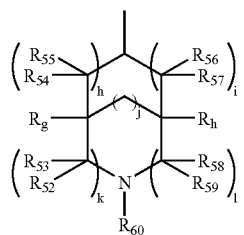

wherein h, i, j, k and l are independently 0 or 1;

$R_{52}$, $R_{53}$, $R_{54}$, $R_{55}$, $R_{56}$, $R_{57}$, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom; and $R_{60}$ is H, substituted or unsubstituted azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolyl alkyl, substituted or unsubstituted pyrimidinyl alkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl; or $R_{60}$ is of the formula

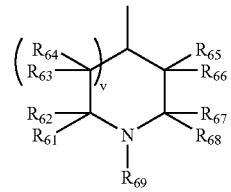

wherein v is 0 or 1;

$R_{61}$, $R_{62}$, $R_{63}$, $R_{64}$, $R_{65}$, $R_{66}$, $R_{67}$ and $R_{68}$ are each, independently, lower alkyl or hydrogen; or at least one pair of substituents $R_{61}$ and $R_{62}$; $R_{63}$ and $R_{64}$; $R_{65}$ and $R_{66}$; and $R_{67}$ and $R_{68}$ together are an oxygen atom; and $R_{69}$ is H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted thienylalkyl, substituted or unsubstituted pyridylalkyl, substituted or unsubstituted pyrazolylalkyl, substituted or unsubstituted isoxazolylalkyl, substituted or unsubstituted thiadiazolylalkyl, substituted or unsubstituted oxadiazolylalkyl, substituted or unsubstituted indazolylalkyl, substituted or unsubstituted furanylalkyl, substituted or unsubstituted pyrrolylalkyl, substituted or unsubstituted imidazolylalkyl, substituted or unsubstituted pyrazolylalkyl, substituted or unsubstituted triazolylalkyl, substituted or unsubstituted pyrimdinylalkyl, substituted or unsubstituted pyrazinylalkyl, substituted or unsubstituted thiazolylalkyl, substituted or unsubstituted isothiazolylalkyl, substituted or unsubstituted oxazolylalkyl, substituted or unsubstituted tetrazolylalkyl, substituted or unsubstituted benzo[b]thienylalkyl, substituted or unsubstituted benzimidazolylalkyl, substituted or unsubstituted benzoxazolylalkyl, substituted or unsubstituted benzothiazolylalkyl, substituted or unsubstituted benzothiadiazolylalkyl, substituted or unsubstituted benzodiazolylalkyl, substituted or unsubstituted indolylalkyl, substituted or unsubstituted tetrahydroindolylalkyl, substituted or unsubstituted azaindolylalkyl, substituted or unsubstituted indazolylalkyl, substituted or unsubstituted quinolinylalkyl, substituted or unsubstituted imidazopyridinylalkyl, substituted or unsubstituted quinazoline purinylalkyl, substituted or unsubstituted pyrrolo[2,3-d]pyrimidinylalkyl or substituted or unsubstituted pyrazolo[3,4-d]pyrimidinylalkyl.

33. A compound according to claim 1, wherein $R_3$ is H; $R_2$ is -$Z^{101}$-$Z^{102}$ where $Z^{101}$ is a covalent bond, straight chained, branched or cyclic hydrocarbon which is completely saturated or which contains one or more units of unsaturation, (straight chained, branched or cyclic hydrocarbon which is completely saturated or which contains one or more units of unsaturation)-O—, (straight chained, branched or cyclic hydrocarbon which is completely saturated or which contains one or more units of unsaturation)-C(O)—, (straight chained, branched or cyclic hydrocarbon which is completely saturated or which contain one or more units of unsaturation)-C(O)O—, straight chained, branched or cyclic hydrocarbon which is completely saturated or which contains one or more units of unsaturation)-C(O)—NH—, (straight chained, branched or cyclic hydrocarbon which is completely saturated or which contains one or more units of unsaturation)-C(O)—N (straight chained, branched or cyclic hydrocarbon which is completely saturated or which contains one or more units of unsaturation)) or a substituted phenyl group; and $Z^{102}$ is hydrogen, a substituted or unsubstituted alkyl group or a substituted or unsubstituted, thienyl, substituted or unsubstituted pyridyl, substituted or unsubstituted pyrazolyl, substituted or unsubstituted isoxazolyl, substituted or unsubstituted thiadiazolyl, substituted or unsubstituted oxadiazolyl, substituted or unsubstituted indazolyl, substituted or unsubstituted furanyl, substituted or unsubstituted pyrrolyl, substituted or unsubstituted imidazolyl, substituted or unsubstituted pyrazolyl, substituted or unsubstituted triazolyl, substituted or unsubstituted pyrimidinyl, substituted or unsubstituted pyrazinyl, substituted or unsubstituted thiazolyl, substituted or unsubstituted isothiazolyl, substituted or unsubstituted oxazolyl, substituted or unsubstituted tetrazolyl, substituted or unsubstituted benzo[b]thienyl, substituted or unsubstituted benzimidazolyl, substituted or unsubstituted benzoxazolyl, substituted or unsubstituted benzothiazolyl, substituted or unsubstituted benzothiadiazolyl, substituted or unsubstituted benzodiazolyl, substituted or unsubstituted indolyl, substituted or unsubstituted tetrahydroindolyl, substituted or unsubstituted azaindolyl, substituted or unsubstituted indazolyl, substituted or unsubstituted quinolinyl, substituted or unsubstituted imidazopyridinyl, substituted or unsubstituted quinazoline purinyl, substituted or unsubstituted pyrrolo[2,3-d]pyrimidinyl, substituted or unsubstituted pyrazolo[3,4-d]pyrimidinyl group.

34. A compound according to claim 33, wherein $Z^{101}$ is selected from the group consisting of —$CH_2$—C(O)O—, —$CH_2$—C(O)—, —$CH_2$—C(O)—NH—, —$CH_2$—C(O)—N(Me)—, —CH(Me)—C(O)O—, —$(CH_2)_3$—C(O)O—, —CH(Me)—C(O)—NH—, and —$(CH_2)_3$—C(O)—NH—;

$Z^{102}$ is selected from the group consisting of hydrogen, methyl, ethyl, N,N-dimethylaminoethyl, N,N-diethylaminoethyl, 2-phenyl-2-hydroxyethyl, morpholino, piperazinyl, N-methylpiperazinyl and 2-hydroxymethylpyrrolidinyl.

35. A compound according to claim 34, wherein $R_1$ is

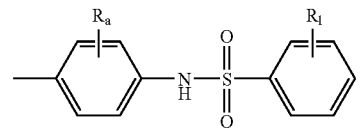

or

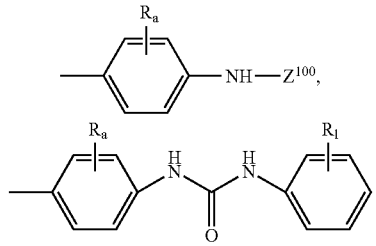

where $Z^{100}$ is a substituted or unsubstituted benzoxazolyl or a substituted or unsubstituted benzthiazolyl.

36. A compound according to claim 8, 9, 10 or 34, wherein $R_1$ is

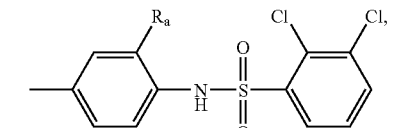

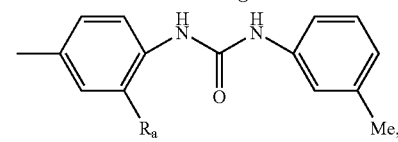

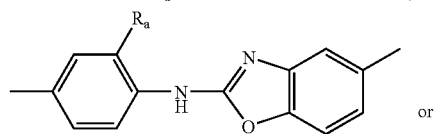

or

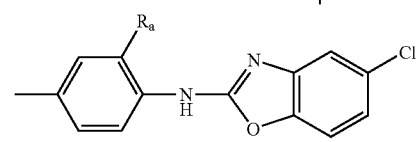

where there is only one $R_a$ and it is H or F.

37. A compound according to claim 33, wherein $Z^{101}$ is a covalent bond;
and $Z^{102}$ is an optionally substituted pyridyl.

38. A compound according to claim 37, wherein $R_1$ is

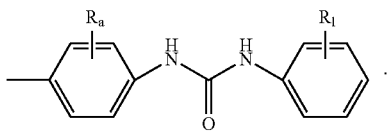

39. A compound according to claim 1, wherein $R_3$ is H; $R_2$ is cyclopentyl; and $R_1$ is

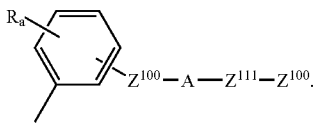

40. A compound according to claim 39, wherein
$Z^{110}$ is hydrogen;
A is O; and $Z^{100}$ is optionally substituted phenyl, furanyl or thienyl, where $Z^{100}$ is optionally substituted with one or more substituents each independently selected from the group consisting of F, COOH, $NO_2$, OMe, —COOMe, $OCF_3$ and $CF_3$.

41. A compound according to claim 39, wherein
$Z^{110}$ is hydrogen;
A is —O—, —O—$(CR_2)_n$—C(O)— or —O—$(CR_2)_n$—O—;
n for each occurrence is 0 to 3;
$Z^{100}$ is an optionally substituted group selected from the group consisting of cyclohexyl, phenyl, tetrahydropyranyl, tetrahydrofuranyl, isoxazolyl and piperidinyl; where $Z^{100}$ is optionally substituted with one or more substituents selected from the group consisting of alkyl, alkoxy, halo, hydroxy and alkoxycarbonyl.

42. A compound according to claim 39, wherein $R^2$ is an optionally substituted group selected from the group consisting of cyclobutyl and cyclohexyl.

43. A compound according to claim 42, wherein $R^2$ is optionally substituted with one or more substituents selected from the group consisting of hydroxy, alkyl, hydroxyalkyl, carboxyalkyl and phenylalkoxyalkyl.

44. A compound according to claim 43, wherein $R_1$ is 4-phenoxyphenyl.

45. A compound according to claim 6 wherein
m is 2; a is 0; $R_6$ is H; b is 1 or 2; and $R_4$ and $R_5$ are each hydrogen.

46. A compound according to claim 8, wherein
m is 0, 1 or 2; $R_6$ is hydrogen; $R_5$ is H or Y-Z;
where Y is a covalent bond, —C(O)—, —$(CH_2)_qO$—, —$(CH_2)_q$—, —$(CH_2)_qC(O)$— or —$C(O)(CH_2)_q$—,
where the alkyl portion of —$(CH_2)_qO$—, —$(CH_2)_p$—, —$(CH_2)_qC(O)$— and —$C(O)(CH_2)_q$— is optionally substituted by a halogen, hydroxy or an alkyl group; and
Z is hydrogen, alkyl, optionally substituted alkyl, alkoxyalkyl, optionally substituted thienylalkyl, optionally substituted pyridylalkyl, optionally substituted pyrazolylalkyl, optionally substituted isoxazolylalkyl, optionally substituted thiadiazolylalkyl, optionally substituted oxadiazolylalkyl, optionally substituted indazolylalkyl, optionally substituted furanylalkyl, optionally substituted pyrrolylalkyl, optionally substituted imidazolylalkyl, optionally substituted pyrazolylalkyl, optionally substituted triazolylalkyl, optionally substituted pyrimidinylalkyl, optionally substituted pyrazinylalkyl, optionally substituted thiazolylalkyl, optionally substituted isothiazolylalkyl, optionally substituted oxazolylalkyl, optionally substituted tetrazolylalkyl, optionally substituted benzo[b]thienylalkyl, optionally substituted benzimidazolylalkyl, optionally substituted benzoxazolylalkyl, optionally substituted benzothiazolylalkyl, optionally substituted benzothiadiazolylalkyl, optionally substituted benzodiazolylalkyl, optionally substituted indolylalkyl, optionally substituted tetrahydroindolylalkyl, optionally substituted azaindolylalkyl, optionally substituted indazolylalkyl, optionally substituted quinolinylalkyl, optionally substituted imidazopyridinylalkyl, optionally substituted quinazoline purinylalkyl, optionally substituted pyrrolo[2,3-d]pyrimidinylalkyl, optionally substituted pyrazolo[3,4-d]pyrimidinylalkyl, optionally substituted heteroaryl, or optionally substituted amino.

47. A compound according to claim 46, wherein
Z is hydrogen, methyl, ethyl, hydroxymethyl, methoxyethyl, N-methyl-piperidinyl, (t-butoxycarbonyl)(hydroxy)-piperidinyl, hydroxypiperidinyl, (hydroxymethyl)piperdinyl, (hydroxy)(methyl)-piperidinyl, morpholino, (methoxyethyl)piperizinyl, methylpiperizinyl, 4-piperidinylpiperidinyl, imidazolyl, methylimidazolyl, N-methylamino, N,N-dimethylamino, N-isopropylamino, N,N-diethylamino, 2,3-dihydroxypropylamino, 2-hydroxyethylamino, 3-hydroxypropylamino, methoxyethylamino, ethoxycarbonylmethylamino, phenylmethylamino, N-methyl-N-methoxyamino,

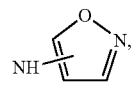

furanylmethylamino, piperidinylethylamino, N-(2-N, N-dimethylaminoethyl)-N-methylamino, 2-N,N-dimethylaminoethylamino, N-methyl-N-(N-methylpiperidin-4-yl)amino, 2-morpholino-ethylamino, 3-morpholino-propylamino, 3-imidazolylpropylamino, or 3-(2-oxopyrrolidinyl)propylamino.

48. A compound according to claim 8, wherein m is 2; $R_5$ is Y-Z; Y is —C(O)—; and Z is

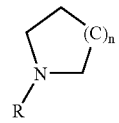

where n is 0, 1, 2 or 3.

49. A compound according to claim 9, wherein
$R_4$ is hydrogen or methyl;
$R_1$ is

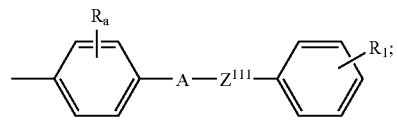

A is selected from the group consisting of O, —N(R)— and —N(R)C(O)—;

$Z^{111}$ is —(CH$_2$)$_n$-cycloalkyl-(CH$_2$)$_n$—;

R is hydrogen or alkyl;

n is 0 to 5;

$R_a$ is one or more substituents each independently selected from the group consisting of H, OH, F, Cl, methyl and methoxy; and $R_b$ is one or more substituents each independently selected from the group consisting of H, CN, F, CF$_3$, OCF$_3$, methyl, methoxy and an optionally substituted amino group;

where said amino group is optionally substituted with one or two groups each independently selected from the group consisting of alkyl, alkoxyalkyl, phenyl, substituted phenyl, and optionally substituted heteroaryl.

50. A compound according to claim 49, wherein $R_b$ is 4-methylphenylthio or 2-pyridinylthio.

51. A compound according to claim 9, wherein $R_1$ is

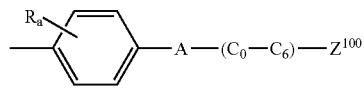

where $Z^{100}$ is selected from the group consisting of benzo[b]thiophene, furanyl and thiophene.

52. A compound according to claim 9, wherein $R_a$ is alkoxy; A is —NH—C(O)—; and there is a covalent bond between A and $Z^{100}$.

53. A compound according to claims 1, 8 or 9, wherein $R_1$ is

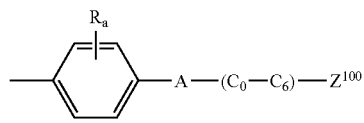

A is selected from the group consisting of —N(R)—C(O)—N(R)—, —(CH$_2$)$_n$—N(R)C(O)N(R)—, —N(R)— and —N(R)—SO$_2$—; R is hydrogen or alkyl;

$Z^{100}$ is

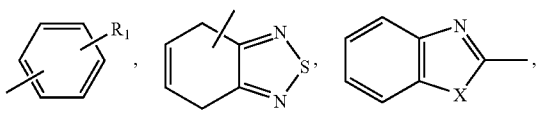

pyridinyl, thiazolyl, furanyl, benzofuranyl or oxazolyl; X is S, O or NR where R for each occurrence is independently H or Me;

$R_a$ is one or more substituents each independently selected from the group consisting of H and F; and $R_b$ is one or more substituents each independently selected from the group consisting of H, F, Cl, Br, NO$_2$, CF$_3$, alkyl, alkoxy and alkoxycarbonyl.

54. A compound according to claim 53, wherein $R_4$ is methyl; m is 1, 2 or 3; $R_5$ is Y-Z, where Y is —C(O)O—, —C(O)— or —C(O)—(CH$_2$)$_p$—; and Z is aminoalkyl, N-alkylamino, N,N-dialkylamino or hydroxyalkylaminoalkyl.

55. A compound according to claim 9, wherein $R_4$ is methyl; $R_1$ is

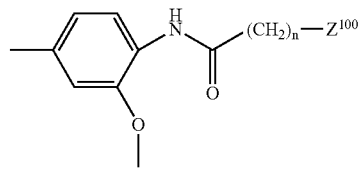

where n is 0 to 3; $Z^{100}$ is an optionally substituted group selected from the group consisting of indolyl, indenyl, methylindenyl, methylindolyl, dimethylaminophenyl, phenyl, cyclohexyl and benzofuranyl.

56. A compound according to claim 9, wherein $R_1$ is

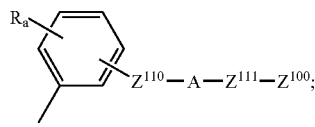

$Z^{100}$ is an optionally substituted group selected from the group consisting of phenyl, imidazolyl, indolyl, furanyl, benzofuranyl and 2,3-dihydrobenzofuranyl;

where $Z^{100}$ is optionally substituted with one or more substituents each independently selected from the group consisting of F, Cl, CN, optionally substituted alkyl, —O-(optionally substituted alkyl), —COOH, -$Z^{105}$-C(O)N(R)$_2$, -$Z^{105}$-N(R)—C(O)-$Z^{200}$, -$Z^{105}$-N(R)—S(O)$_2$-$Z^{200}$, and -$Z^{105}$-N(R)—C(O)—N(R)-$Z^{200}$;

$Z^{105}$ is a covalent bond or (straight chained, branched or cyclic hydrocarbon which is completely saturated or which contains one or more units of unsaturation);

$Z^{200}$ is an optionally substituted group selected from group consisting of (straight chained, branched or cyclic hydrocarbon which is completely saturated or which contains one or more units of unsaturation), phenyl and straight chained, branched or cyclic hydrocarbon which is completely saturated or which contains one or more units of unsaturation) phenyl;

$Z^{110}$ and $Z^{111}$ are each independently a covalent bond or (C$_1$–C$_3$)straight chained, branched or cyclic hydrocarbon which is completely saturated or which contains one or more units of unsaturation group optionally substituted with alkyl, hydroxy, COOH, CN or phenyl; and A is O, —N(R)—C(O)—N(R)—, —N(R)—C(O)—O—, —N(R)— or —N(R)—C(O)—, where R is H or alkyl.

57. A compound according to claim 56, wherein $R_4$ is methyl.

58. A compound according to claim 8, 9 or 10, wherein $R_1$ is

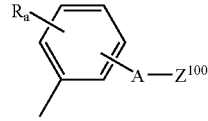

where $Z^{100}$ is an optionally substituted group selected from the group consisting of benzoxazolyl, benzothiazolyl and benzimidazolyl.

59. A compound according to claim 58, wherein $R_4$ is methyl; A is —NH—;
there is only one $R_a$ and it is H or F; and $Z^{100}$ is optionally substituted with one or more substituents each independently selected from the group consisting of alkyl, halo, $CF_3$, and alkoxy.

60. A compound according to claim 9, wherein $R_1$ is

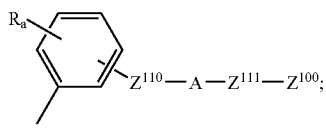

$Z^{100}$ is an optionally substituted group selected from the group consisting of phenyl, pyrrolyl, pyridyl, benzimidazolyl, naphthyl and

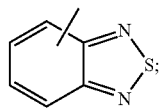

where $Z^{100}$ is optionally substituted with one or more substituents each independently selected from the group consisting of F, Cl, Br, $NO_2$, amino, N-alkylamino, N,N-dialkylamino, CN, optionally substituted alkyl, —O-(optionally substituted alkyl) and phenyl;

$Z^{110}$ and $Z^{111}$ for each occurrence is independently ($C_0$—$C_3$) optionally substituted with optionally substituted phenyl; and A is —N(R)—C(O)—N(R)—, —N(R)—S(O)$_2$—, —N(R)—C(O)—, —N(R)— or —N(R)—C(O)—O—.

61. A compound according to claim 60, wherein $R_4$ is methyl and there is only one $R_a$ and it is F.

62. A compound according to claim 9 or 47, wherein $R_1$ is

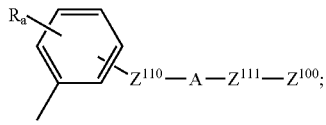

$Z^{100}$ is an optionally substituted group selected from the group consisting of phenyl, isoxazolyl, tetrahydronaphthyl, furanyl, benzofuranyl, pyridyl and indolyl;
where $Z^{100}$ is optionally substituted with one or more substituents each independently selected from the group consisting of F, CN, $NO_2$, —C(O)H, —CONH$_2$, —NHSO$_2$CF$_3$, optionally substituted alkyl, optionally substituted heteroaryl and —O-(optionally substituted alkyl);

$Z^{110}$ and $Z^{111}$ are each independently optionally substituted ($C_0$–$C_3$); and A is O, —N(R)—C(O)—(CH$_2$)$_n$—N(R)—, —C(O)—N(R)—, —N(R)—C(O)—O—, —N(R)—C(O)— or —N(R)—.

63. A compound according to claim 62, wherein $R_4$ is methyl; $R_a$ is H or methoxy; and $Z^{110}$ and $Z^{111}$ are each unsubstituted.

64. A compound according to claim 9, wherein $R_1$ is

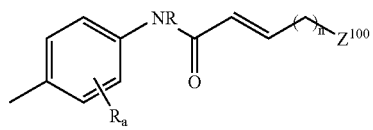

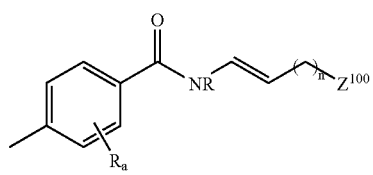

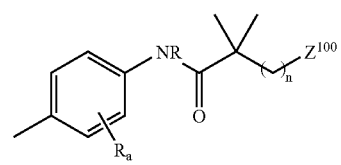

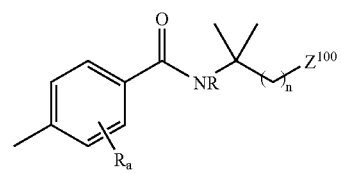

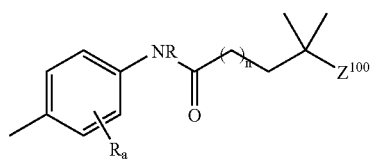

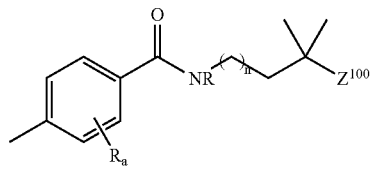

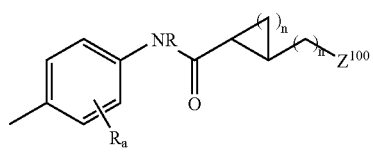

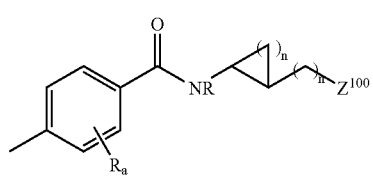

-continued

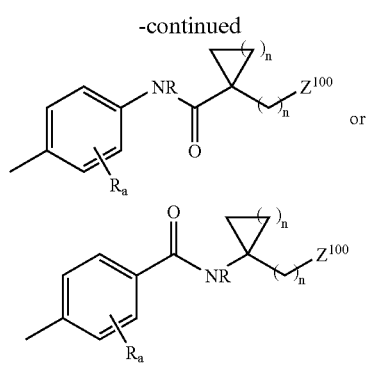

or

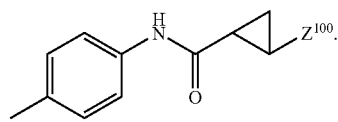

where R is H or lower alkyl and n is for each occurrence is independently 1 to 6.

65. A compound according to claim 64, wherein $R_1$ is

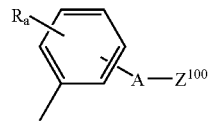

66. A compound according to claim 65, wherein $Z^{100}$ is substituted or unsubstituted phenyl.

67. A compound according to claim 8, 9 or 10, wherein $R_1$ is where $Z^{100}$ is an optionally substituted group selected from the group consisting of benzoxazolyl, benzothiazolyl and benzimidazolyl.

68. A compound according to claim 11 wherein n is 2; $R_6$ is H; m is 1; r is 1; and $R_4$ and $R_5$ are each hydrogen.

69. A compound according to claim 45 or 68 wherein $R_1$ is 4-phenoxyphenyl.

* * * * *

UNITED STATES PATENT AND TRADEMARK OFFICE
CERTIFICATE OF CORRECTION

PATENT NO.       : 7,071,199 B1
APPLICATION NO.  : 09/663320
DATED            : July 4, 2006
INVENTOR(S)      : Gavin C. Hirst et al.

It is certified that error appears in the above-identified patent and that said Letters Patent is hereby corrected as shown below:

Column 98, line 33 – remove ";"

Column 99, line 29 – remove "," before "thienyl"

Column 99, line 52 – add --,-- after "quinazoline"

Column 102, line 12 – change "pyrimdinyl" to --pyrimidinyl--

Column 102, line 18 – add --,-- after "N-oxides"

Column 102, line 30 – change "pyrimdinyl" to --pyrimidinyl--

Column 103, line 26 – change "pyrimdinyl" to --pyrimidinyl--

Column 105, line 38 – change "pyrimdinyl" to --pyrimidinyl--

Column 107, line 49 – change "pyrimdinyl" to --pyrimidinyl--

Column 109, line 3 – change "pyrimdinyl" to --pyrimidinyl--

Column 111, line 13 – change "pyrimdinyl" to --pyrimidinyl--

Column 112, line 43 – change "pyrimdinyl" to --pyrimidinyl--

Column 114, line 17 – change "pyrimdinyl" to --pyrimidinyl--

Column 116, line 6 – change "pyrimdinyl" to --pyrimidinyl--

Column 117, line 31 – change "pyrimdinyl" to --pyrimidinyl--

Column 119, line 2 –  change "pyrimdinyl" to --pyrimidinyl--

Column 119, lines 61-62 – delete "substituted or unsubstituted pyrazolyl,"

Column 123, line 10 -  delete "substituted or unsubstituted pyrazolylalkyl"

Column 124, line 2 -  delete "substituted or unsubstituted pyrazolylalkyl"

Column 124, line 51 –  change "pyrimdinylalkyl" to --pyrimidinylalkyl--

Column 125, line 46-47 –  delete "substituted or unsubstituted pyrazolyl,"

UNITED STATES PATENT AND TRADEMARK OFFICE
CERTIFICATE OF CORRECTION

PATENT NO.       : 7,071,199 B1
APPLICATION NO.  : 09/663320
DATED            : July 4, 2006
INVENTOR(S)      : Gavin C. Hirst et al.

It is certified that error appears in the above-identified patent and that said Letters Patent is hereby corrected as shown below:

Column 126, line 36 – change "benzthiazolyl" to --benzothiazolyl--

Column 127, line 65 – delete "optionally substituted pyrazolylalkyl"

Column 128, line 21-22 – change "(hydroxymethyl)piperdinyl" to --(hydroxymethylpiperidinyl--

Column 130, line 44 – insert --(-- before "straight"

Column 130, line 47 – insert -- - -- after "unsaturation)" and before "phenyl;"

Signed and Sealed this

Twelfth Day of June, 2007

JON W. DUDAS
*Director of the United States Patent and Trademark Office*